US009280726B2

(12) United States Patent
Dorris et al.

(10) Patent No.: US 9,280,726 B2
(45) Date of Patent: Mar. 8, 2016

(54) ON-LINE MACROCONTAMINANT ANALYSER AND METHOD

(75) Inventors: Gilles Marcel Dorris, Vimont, Laval (CA); Carlos Castro Caloca, Mirabel (CA); Sylvain Gendron, Montreal (CA); Michelle Agnes Ricard, Pointe-des-Cascades (CA); Natalie Pagé, Laval (CA); Denise Filion, St-Isidore de Laprairie (CA)

(73) Assignee: FPINNOVATION, St-Jean, Pointe-Claire, Quebec (CA)

( * ) Notice: Subject to any disclaimer, the term of this patent is extended or adjusted under 35 U.S.C. 154(b) by 873 days.

(21) Appl. No.: 13/516,858

(22) PCT Filed: Dec. 17, 2010
(Under 37 CFR 1.47)

(86) PCT No.: PCT/CA2010/002019
§ 371 (c)(1),
(2), (4) Date: Nov. 27, 2012

(87) PCT Pub. No.: WO2011/072396
PCT Pub. Date: Jun. 23, 2011

(65) Prior Publication Data
US 2013/0120556 A1      May 16, 2013

Related U.S. Application Data

(60) Provisional application No. 61/287,883, filed on Dec. 18, 2009.

(51) Int. Cl.
*G06K 9/78* (2006.01)
*G01N 21/85* (2006.01)
(Continued)

(52) U.S. Cl.
CPC ........ *G06K 9/78* (2013.01); *G01N 21/85* (2013.01); *G01N 33/343* (2013.01); *C02F 2103/28* (2013.01); *C02F 2209/00* (2013.01)

(58) Field of Classification Search
None
See application file for complete search history.

(56) References Cited

U.S. PATENT DOCUMENTS

| 3,359,786 A | 12/1967 | Von Alfthan |
| 3,830,569 A | 8/1974 | Meric |

(Continued)

FOREIGN PATENT DOCUMENTS

| CA | 1258898 | 8/1989 |
| CA | 2205542 | 6/1996 |

(Continued)

OTHER PUBLICATIONS

International Search Report of PCT/CA2010/002019.

(Continued)

*Primary Examiner* — Michael Teitelbaum
(74) *Attorney, Agent, or Firm* — Norton Rose Fulbright Canada LLP

(57) ABSTRACT

An on-line automated analyzer of macrocontaminants is described. The analyzer is for a pulp and/or a white water stream, the analyzer comprises: a pulp classifier separating a sample from the stream into a fraction of macrocontaminants; a contaminant chamber enclosing a contaminant cell receiving the fraction; an optical chamber comprising an optical detector connected to the cell capturing at least one detected image; and a control chamber taking the at least one detected image and conducting an image analysis to determine type and quantity of at least one macrocontaminant in the fraction. The method of analysis of macrocontaminants is also described herein, the method comprises: separating a sample from the stream into a fraction of macrocontaminants; producing at least one detected image by optical measurement of the fraction; and analyzing the at least one detected image and determining the quantity and type of at least one macrocontaminant in the fraction.

13 Claims, 10 Drawing Sheets

(51) Int. Cl.
*G01N 33/34* (2006.01)
*C02F 103/28* (2006.01)

(56) References Cited

U.S. PATENT DOCUMENTS

| | | | |
|---|---|---|---|
| 4,021,117 A | 5/1977 | Gohde et al. | |
| 4,037,966 A | 7/1977 | Hill | |
| 4,066,492 A | 1/1978 | Hill | |
| 4,220,499 A | 9/1980 | Hughes, Jr. et al. | |
| 4,225,385 A | 9/1980 | Hughes, Jr. et al. | |
| 4,325,706 A | 4/1982 | Gershman et al. | |
| 4,468,954 A | 9/1984 | Lanctot et al. | |
| 4,758,308 A * | 7/1988 | Carr | 162/263 |
| 4,897,159 A | 1/1990 | Bone et al. | |
| 5,006,986 A | 4/1991 | Inoue | |
| 5,141,609 A | 8/1992 | Sweedler et al. | |
| 5,159,642 A | 10/1992 | Kosaka | |
| 5,260,764 A | 11/1993 | Fukuda et al. | |
| 5,486,904 A | 1/1996 | Horn et al. | |
| 5,518,584 A | 5/1996 | Aikawa | |
| 5,542,542 A | 8/1996 | Hoffmann et al. | |
| 5,548,395 A | 8/1996 | Kosaka | |
| 5,627,643 A | 5/1997 | Birnbaum et al. | |
| 5,754,291 A | 5/1998 | Kain | |
| 5,760,900 A | 6/1998 | Ito et al. | |
| 5,786,894 A | 7/1998 | Shields et al. | |
| 5,817,519 A | 10/1998 | Zelmanovic et al. | |
| 5,831,723 A | 11/1998 | Kubota et al. | |
| 5,940,177 A | 8/1999 | Esser et al. | |
| 6,025,201 A | 2/2000 | Zelmanovic et al. | |
| 6,114,173 A | 4/2000 | Zelmanovic et al. | |
| 6,218,121 B1 | 4/2001 | Simpson et al. | |
| 6,236,945 B1 | 5/2001 | Simpson et al. | |
| 6,249,341 B1 | 6/2001 | Basiji et al. | |
| 6,311,550 B1 | 11/2001 | Lehmikangas et al. | |
| 6,421,121 B1 | 7/2002 | Haavig et al. | |
| 6,473,176 B2 | 10/2002 | Basiji et al. | |
| 6,592,822 B1 | 7/2003 | Chandler | |
| 6,613,210 B1 | 9/2003 | Hassard et al. | |
| 6,657,713 B2 | 12/2003 | Hansen | |
| 6,671,044 B2 | 12/2003 | Ortyn et al. | |
| 6,713,264 B2 | 3/2004 | Luttermann et al. | |
| 6,825,921 B1 | 11/2004 | Modlin et al. | |
| 6,838,051 B2 | 1/2005 | Marquiss et al. | |
| 6,838,289 B2 | 1/2005 | Bell et al. | |
| 6,841,390 B1 | 1/2005 | Banerjee | |
| 6,881,587 B2 | 4/2005 | Yogi et al. | |
| 6,970,243 B2 | 11/2005 | Togawa | |
| 6,975,400 B2 | 12/2005 | Ortyn et al. | |
| 7,046,357 B2 | 5/2006 | Weinberger et al. | |
| 7,061,595 B2 | 6/2006 | Cabuz et al. | |
| 7,087,877 B2 | 8/2006 | Ortyn et al. | |
| 7,116,407 B2 | 10/2006 | Hansen et al. | |
| 7,190,832 B2 | 3/2007 | Frost et al. | |
| 7,199,879 B2 | 4/2007 | Harju et al. | |
| 7,283,229 B2 | 10/2007 | Noguchi et al. | |
| 7,300,800 B2 | 11/2007 | Bell et al. | |
| 7,315,357 B2 | 1/2008 | Ortyn et al. | |
| 7,384,503 B2 | 6/2008 | Hoffmann et al. | |
| 7,402,131 B2 | 7/2008 | Mueth et al. | |
| 7,420,659 B1 | 9/2008 | Cabuz et al. | |
| 7,423,751 B2 | 9/2008 | Hairston et al. | |
| 7,425,252 B2 | 9/2008 | Sideris | |
| 7,425,421 B2 | 9/2008 | Dertinger | |
| 7,426,027 B2 | 9/2008 | Noguchi et al. | |
| 7,428,047 B2 | 9/2008 | Oldham et al. | |
| 7,450,235 B1 | 11/2008 | Said et al. | |
| 7,494,809 B2 | 2/2009 | Nelson et al. | |
| 7,497,934 B2 | 3/2009 | Sideris | |
| 7,522,758 B2 | 4/2009 | Ortyn et al. | |
| 7,525,660 B2 | 4/2009 | Gigioli et al. | |
| 7,553,453 B2 | 6/2009 | Gu et al. | |
| 7,554,663 B2 | 6/2009 | Hairston et al. | |
| 7,564,541 B2 | 7/2009 | Tuschel | |
| 2003/0058280 A1 * | 3/2003 | Molinari et al. | 345/771 |
| 2003/0142310 A1 | 7/2003 | Bedard et al. | |
| 2005/0105077 A1 | 5/2005 | Padmanabhan et al. | |
| 2008/0283206 A1 | 11/2008 | Doshi et al. | |
| 2008/0308241 A1 | 12/2008 | Di Cesare | |
| 2009/0084510 A1 | 4/2009 | Perry et al. | |
| 2009/0301674 A1 * | 12/2009 | Niinimaki et al. | 162/49 |

FOREIGN PATENT DOCUMENTS

| | | |
|---|---|---|
| CA | 2631709 | 7/2007 |
| WO | 2007122289 | 11/2007 |
| WO | 2009073145 | 6/2009 |

OTHER PUBLICATIONS

Castro, C. and Dorris, G.M. Measuring microstickies deposition by monitoring pressure drop through a collector. Progr. Pap. Recyc., 13(3):23-33 (2004).

Sitholé, B. and Filion, D. Assessment of methods for the measurement of macrostickies in recycled pulps. Progr. Pap. Recyc., 17(2):16-25 (2008).

Tappi.Macro stickies content in pulp: the pick-up method (1999).

Doshi, M.R. A review of stickies measurement methods. Progr. Pap. Recyc., 18(3):21-32 (2009).

Dorris, G. and Castro, C., Automation of a microstickies deposition tester relating the rate of deposition to the pressure drop across a collector, Presented at the 94th PAPTAC Annual Meeting, Montreal, Feb. 5-7. p. (2008).

Monte, M.C., Blanco, A., Negro, C. and Tijero, J. Development of a methodology to predict sticky deposits due to the destabilisation of dissolved and colloidal material in papermaking—application to different systems. Chemical Engineering Journal, 105:21-29 (2004).

Pelton, R. and Lawrence, D. A new laboratory approach for evaluating kraft mill pitch deposit control additives. J. Pulp Pap. Sci., 17(3):J80-J84 (1991).

Sitholé, B., Filion, D. and Allen, L.H. A laboratory test to measure deposition in recycled paper making. Paper Technology, 40(1):26-30 (1999).

Ricard, M. and Dorris, G.M., Recirculation contaminates whitewater solids Part II: Contamination of fines and fillers by extractives and metals, Presented at the 93rd PAPTAC Annual Meeting, Montreal. p. B263-B270. PAPTAC (2007).

Ruuska, M., Tirronen, V. and Launonen, U. Unified on-line dirt count and process disturbance analysis system for pulp applications. Appita Journal, 61(6) (2008).

* cited by examiner

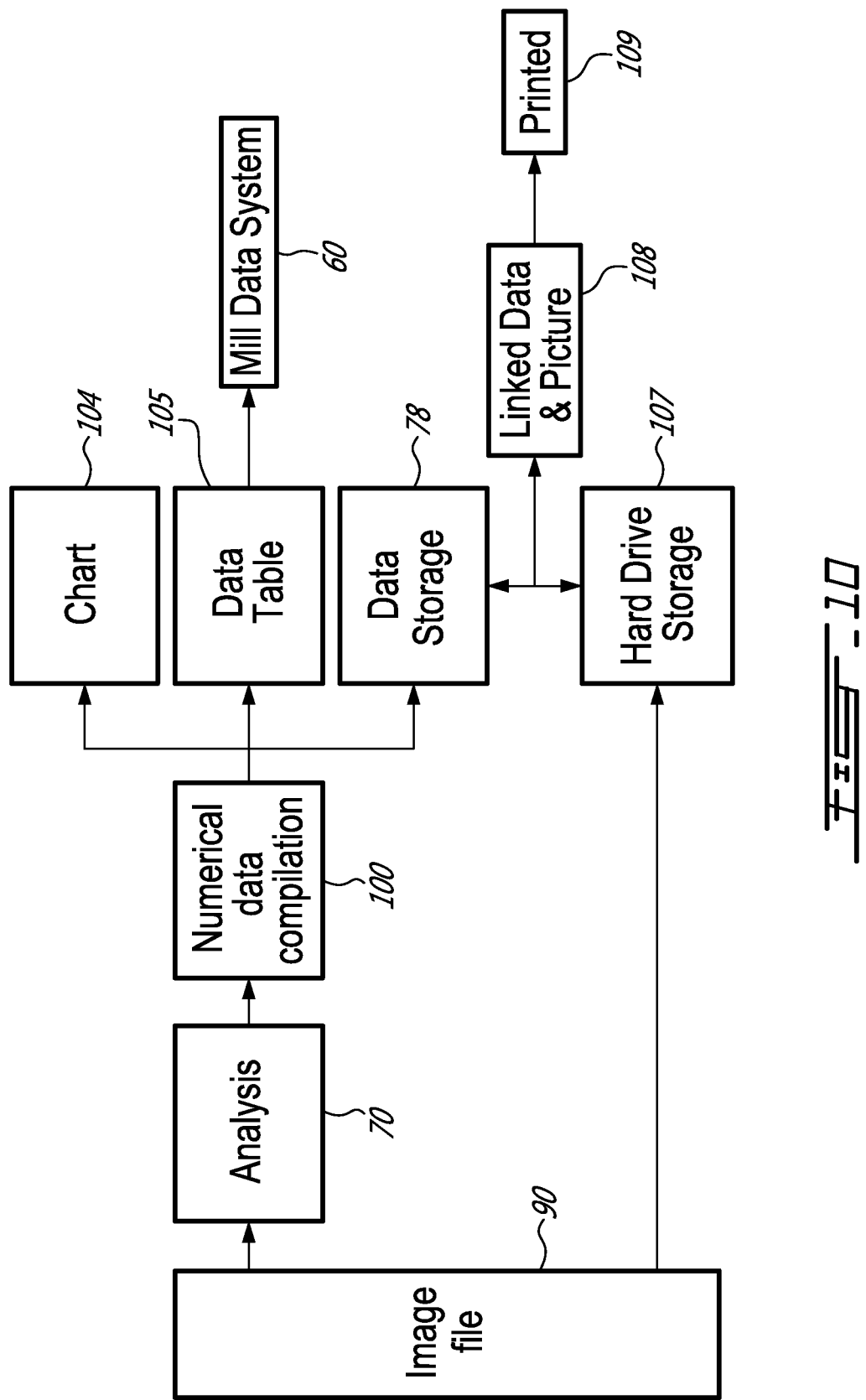

ON-LINE MACROCONTAMINANT ANALYSER AND METHOD

CROSS-REFERENCE TO RELATED APPLICATIONS

This application is a National entry of PCT/CA2010/002019 filed Dec. 17, 2010, in which the United States of America was designated and elected, and which remains pending in the International phase until Jun. 18, 2012, which application in turn claims priority under 35 USC 119(e) from U.S. Provisional Application Ser. No. 61/287,883, filed Dec. 18, 2009.

FIELD OF THE INVENTION

The present invention relates to an on-line automated analyser of macrocontaminants and a method of analysing macrocontaminants in pulp.

BACKGROUND ART

Contaminants represent undesirable components in a pulp suspension or in white waters because they may hamper manufacturing operations or quality of pulp, paper or paper products. Depending on a pre-established size scale, they are classified as macrocontaminants and microcontaminants. It is customary to distinguish macro- from microcontaminants by measuring the amount of material retained on a 0.10 to 0.15 mm slotted screen. Accurate determination of macrocontaminants in pulps and white waters is of utmost importance for pulp and papermakers, chemical suppliers, adhesives manufacturers, printers and researchers.

This measurement of macrocontaminants is particularly useful for a pulp and paper mill because it dictates control and elimination strategies. The nature and amount of contaminants in pulps and water streams depend on the type of pulp manufactured and on the degree of system closure. An example of harmful contaminants in virgin pulp is shines originating from incomplete defiberizing of wood. Stickies are another important class of contaminants so-named because they pertain to materials that have a strong tendency to deposit on or stick to a wide variety of surfaces.

Stickies, which represent by far the most detrimental class of contaminants in recycled pulps, embrace a large variety of lipophilic compounds. They originate from pressure sensitive adhesives (PSAs), hot melts, toner, waxes, coating and binders that are used in labels, tapes, envelopes, stamps, paperboards for a variety of functions like binding, sealing, coating and printing. Adhesives, coatings and waxes, which are introduced in recycling plants with recovered papers, are subjected to intense mechanical action during pulping, screening, pumping, dispersion and kneading. Strong shear forces applied to adhesives during pulp processing and paper manufacturing will lead to their fragmentation into a wide range of particle sizes. The release of sticky substances in the water phase leads to the production of off spec pulp from the drinking plant, increased chemical costs for their passivation and solvent cleaning, poor runability at the paper machine and in press rooms, and poor product quality. Though vital for efficient control of recycling operations macrostickies measurement is infrequent, due to personnel shortages and the tedious nature of the manual methods [Refs: 1-5]. Despite the seriousness of the problem, very few devices have been proposed for on-line monitoring stickies in pulp streams [Refs: 6-10].

One of the biggest hurdles faced in developing an on-line instrument is that the unit must be capable of measuring a small number of contaminants in a pulp mat or in a pulp suspension consisting mainly of fibres. The presence of these fibres impedes proper detection of contaminants, especially when image analysis is used for objects discrimination and quantification. To get around this problem, a wide variety of laboratory methods first separate contaminants prior to their detection, quantification and measurement. The most widely-used laboratory methods use laboratory screens, hydrocyclones, filtration and the like to first isolate the contaminants from the fibre [Refs: 1-5, 10]. Once segregated, the contaminants, such as stickies, dirt, and shines are collected from the screen or deposited on filter paper. Whereas dirt and shives do not require special preparation for their quantification, it is a different matter when the contaminants include stickies. The tacky nature of stickies is used to separate them from other macrocontaminants or to transfer them to an appropriate support where they can be examined visually and counted by eye or with the aid of an image analyser. The preparation of stickies for visual analysis is a tedious procedure that limits the throughput of stickies analysis. Some other instruments are based on the tackiness of the contaminants and their tendency to deposit on paper machine wires and paper [Refs: 2, 11-14]. Although useful, these laboratory tests are all time consuming and without microscopy and/or chemical analysis do not reveal much about the type of contaminant, their area or numbers.

A few patents exist that describe equipment for on-line measurement of small proportion of components in a liquid containing predominantly other components, particularly in the area of detecting white blood cells, platelets or antibodies in blood [Refs; 15-31] and shives in pulp [Refs: 32-43]. Fewer patents refer to the actual on-line measurement of stickies in pulp [Refs: 6-10, 44].

Many of these analysers require dilution of blood or pulp samples to facilitate visualization or detection of the component of interest. Passage through laminar hydrodynamic flow cells then allow component or contaminant identification, measurement or enumeration [Refs: 15, 17-19, 21-32, 34-36, 41-69]. Visualization of white blood cells or platelets in a mass of red blood cells often involve sphering the red blood cells or promoting their removal through cell lysis [Refs: 15, 18, 22, 23, 28, 30, 50, 51, 59], staining of different biological components with fluorescent dyes [Refs: 18-22, 24, 25, 27, 30, 70, 71], or their separation through electrophoresis [Refs: 72-77]. In these systems, particle detection can be made through photodetection of scattered light [Refs: 15, 18, 21-25, 27, 30, 31, 70, 71, 78, 79], near infrared reflectance [Refs: 56, 57] or by image analysis of captured images by charged coupled devices [Refs: 25-27, 49, 52-55, 72, 76, 77, 80-82]. Image analysis is a useful tool that discerns features of individual components and allows their enumeration and measurement [Refs: 25, 80]. Unlike blood cells, pulp fibres, shives or stickies cannot undergo cell lysis to separate white blood cells and platelets from the larger mass of red blood cells. On the other hand, in many respects many of the techniques used to separate, detect and measure white blood cells and platelets can be used for pulp. Sample dilution, hydrodynamic focusing and the use of fluorescent dyes are indeed used in many pulp applications to separate and/or distinguish fibres prior to their photodetection or imaging by charged coupled devices. [Refs: 6, 7, 9, 32, 34, 35, 42-44, 83]. However, when the object of analysis is a large sticky particle, its amount relative to fibres population is so small that a large volume of sample must be processed at a low flow rate in the laminar flow cell in order to detect sufficient amount of stickies to obtain statistically significant counts. This imposes serious limitations to the throughput of an analyser using hydrodynamic focusing. These methods are further described in the following paragraphs.

Compared to blood analysers, shine analysers use pulp dilution, hydrodynamic focusing, screens, hydrocyclones or suction extractor through gaps to separate the shives from the fibre mass prior to analysis of contaminants [Refs: 9, 32, 34-43, 84]. Because shives have wider diameters and higher densities than water, screens and hydrocyclones can isolate shives from the pulp mass. Light is passed through the flow cell and the sample and, the change in light or pulse signal will allow determination of particle or fibre size [Refs: 9, 32, 34-36, 40, 42, 43]. Although useful, the small number of contaminants and their similar color to the fibre hampers their visualization and identification. The same principles that allow shives content determination—higher density than water and greater diameter than fibres—will also facilitate segregation of macrostickies from pulp.

For stickies detection and measurement, four methods using fluorescent dyes to detect hydrophobic components of pulp have been described [Refs: 6-8, 83]. The methods of Horn et al. [7] was designed to detect wood resin particles in pulp. This analyser used the same principles as those analysers described by Esser et al. [8], Di Cesare [6] and Perry et al. [83] except that they are defined as stickies analysers. Each of these instruments use photodetection coupled with the addition of fluorescent dyes to a pulp suspension as a means to identify organic components such as stickies and wood resin in pulp. The fluorescent dye reacts with the hydrophobic contaminants such as stickies. When the fluorescent-dyed components are excited by light at a specified wavelength, the hydrophobic contaminants will emit light which can later be detected by a photodetector. The light emission signals proportional to the size of the contaminant is detected in the photocell and the signals evaluated to measure the hydrophobic contaminants. One of the problems with this method, is that fibres, fines and shives rich in lipophilic extractives such as triglycerides and fatty acids [85] may interfere in the measurement of stickies. Hence, these methods do not distinguish between stickies and pitch because both classes are hydrophobic in nature. Moreover, these methods do not permit enumeration of stickies based on their area or type. All of these four methods use laminar flow cells or hydrodynamic focusing to separate the contaminants and allow their detection. Combining hydrodynamic focusing with a prior contaminant isolation step might give better results such as the method described by Carr [9].

The first stickies analyser was described by Carr [9]. This analyser functions by first diluting the pulp sample to a consistency less than 0.5% and passing the diluted pulp sample through a series of hydrocyclones to separate particles according to their density. The separated particles are then diluted again to a consistency less than 0.5% before passage through a flow cell. The flow is back lighted and a photodetector includes a linear array of sensitive elements aligned to receive the transmitted light. The sensitive elements aligned with particles create a signal proportional to the width. By rapid sequential activation of the elements, a digital data stream is created which is processed by a microprocessor to determine the particle size and produce a plurality of contaminant relative signals related to different classified size ranges, such as heavy, medium and small contaminant particles. The addition of a fluorescent dye could also be added to help identify contaminants in the photocell. If we take a new look at this method over 20 years later, the use of charged coupled devices with added imaging capacities may improve this method. One of the limits of the method is that hydrocyclones are used to separate stickies from pulp. With the exception of waxes and other light-weight macrocontaminants, often macrostickies have a similar density to water, limiting their isolation via hydrocyclones and leading to the presence of fibres in the sample preparation. Another drawback of the method as an on-line device is that it uses hydrodynamic focusing to separate particles in a laminar flow prior to their detection. The sample size that can be handled by such cells is small in the order of milliliters. Passage of liter-sized samples resulting from pulp screening or cleaning methods would limit use of such flow cells.

A method for analyzing very small stickies in pulps has been described by Banerjee [10]. Again screening, albeit through filtration, is used to remove fibres, fibre debris, and other large contaminant particles from the fibre slurry, after which the carbon content of the filtered sample is measured. Next, the filtrate is ultrafiltered to separate stickies having a high molecular weight from the filtrate, and subsequently, the carbon content of the ultrafiltered sample is measured. The filter pore size used in ultrafiltration is of 25 µm. Finally, the carbon contents are used to determine the microstickies concentration in the fibre slurry. Although useful, this method is reported to give an estimate of microstickies content and not that of macrocontaminants such as macrostickies, shines and toner. In principle, other organic material solubilized from wood or arising from paper machine additives, should pass through the pores of 25 µm and not be detected. However, these components tend to form agglomerates in pulp waters that may interfere with this measurement.

Flow cells have been known to measure dark particles or specks such as bark, metal, and toner contaminants present in kraft [84] and recycled pulps (Simpatic, PapTech). Although good for measuring dark contaminants [38, 84], these analysers have trouble detecting contaminants that are not visually very different from the pulp, such as stickies [86].

SUMMARY

It is therefore an aim of the present invention to provide an on-line automated analysis of macrocontaminants present in pulp or white water samples.

The on-line automated analyser first separates the contaminants from the pulp by screening. The isolated contaminants are then automatically transferred to a chamber that allows further separation of the contaminants into light- and heavy-weight categories based on their relative densities in water. The light- and/or heavy-weight contaminants are then imaged, and analyzed for their type, amount, size and projected area.

Image analysis allows detection of the type of contaminants based on their color, size, diameter, and shape.

The data from all the images of the sample are averaged and a report is prepared that includes the total number and area of heavy- and light-weight contaminants. The report can be visualized on the computer screen of the analyser or sent to mill data base and control systems. Data is stored in the processor with a link to the original images of the contaminants. This data storage will also allow the user to view the historic trends of the total number and area of each contaminant type.

Therefore, in accordance with one aspect of the present invention, there is provided an on-line analyser of macrocontaminants for a pulp and/or a white water stream, the analyser comprising: a pulp classifier separating a sample from the stream into a liquid fraction comprising macrocontaminants; a contaminant chamber enclosing a contaminant cell receiving the fraction; an optical chamber comprising an optical detector connected to the cell capturing at least one detected image; and a control chamber taking the at least one detected image and conducting an image analysis to determine type and quantity of at least one macrocontaminant in the fraction.

In accordance with another aspect of the analyser described herein, the optical detector is at least one high definition digital camera producing the detected image from the contaminant cell.

In accordance with yet another aspect of the analyser described herein, the contaminant cell comprises a contaminant settling plate, comprising a coloured background optimizing the quality of the detected image.

In accordance with still another aspect of the analyser described herein, the optical detector is focused on the contaminant settling plate of the contaminant cell.

In accordance with yet still another aspect of the analyser described herein, the optical detector is focused at the surface of the liquid fraction within the contaminant cell.

In accordance with a further aspect of the analyser described herein, the control chamber comprises a computer comprising a software program performing the image analysis and supervising execution of tasks of the analyser.

In accordance with yet a further aspect of the analyser described herein, the software program communicates with a camera dynamic link library, an imaging library, and an OPC server interacting to identify the type and the quantity of macrocontaminants.

In accordance with still a further aspect of the analyser described herein, the OPC server further communicates with PLCs communicating with the pulp classifier, contaminant chamber and the optical chamber.

In accordance with yet still a further aspect of the analyser described herein, the contaminant cell is a clear cylindrical cell comprising a contaminant settling baseplate and an integrated coloured settling plate, the optical detector comprising a first and a second high definition digital camera, wherein the first camera is focused on the integrated coloured settling plate and a second camera is focused on the surface of the liquid fraction, and the control chamber comprises a computer comprising a software program performing the image analysis and supervising execution of tasks of the analyser.

In accordance with one embodiment of the present invention, there is provided a method of analysing macrocontaminants from a pulp and/or white water stream, the method comprising: separating a sample from the stream into a fraction of macrocontaminants; producing at least one detected image by optical measurement of the fraction; and analysing the at least one detected image and determining the quantity and type of at least one macrocontaminant in the fraction.

In accordance with another embodiment of the method described herein, the at least one detected image is produced by a high definition digital camera.

In accordance with yet another embodiment of the method described herein, a first and a second detected image are produced, and the first detected image is focused on light weight macrocontaminants and the second detected image is focused on heavy weight macrocontaminants.

In accordance with still another embodiment of the method described herein, analysing the at least one detected image is with a software program of a computer communicating with a camera dynamic link library, and imaging library and an OPC server, the software program identifying the at least one macrocontaminant.

In accordance with yet still another embodiment of the method described herein, the software program further communicates to control the separating of the sample and the producing the at least one optical image.

BRIEF DESCRIPTION OF THE DRAWINGS

Reference will now be made to the accompanying drawings, showing by way of illustration a particular embodiment of the present invention and in which:

FIG. 10 is a schematic flowsheet of how analysed images are converted to numerical data, graphs, data tables, or stored as an image file to one embodiment of the present invention.

DETAILED DESCRIPTION OF PARTICULAR EMBODIMENTS

Figure 1:
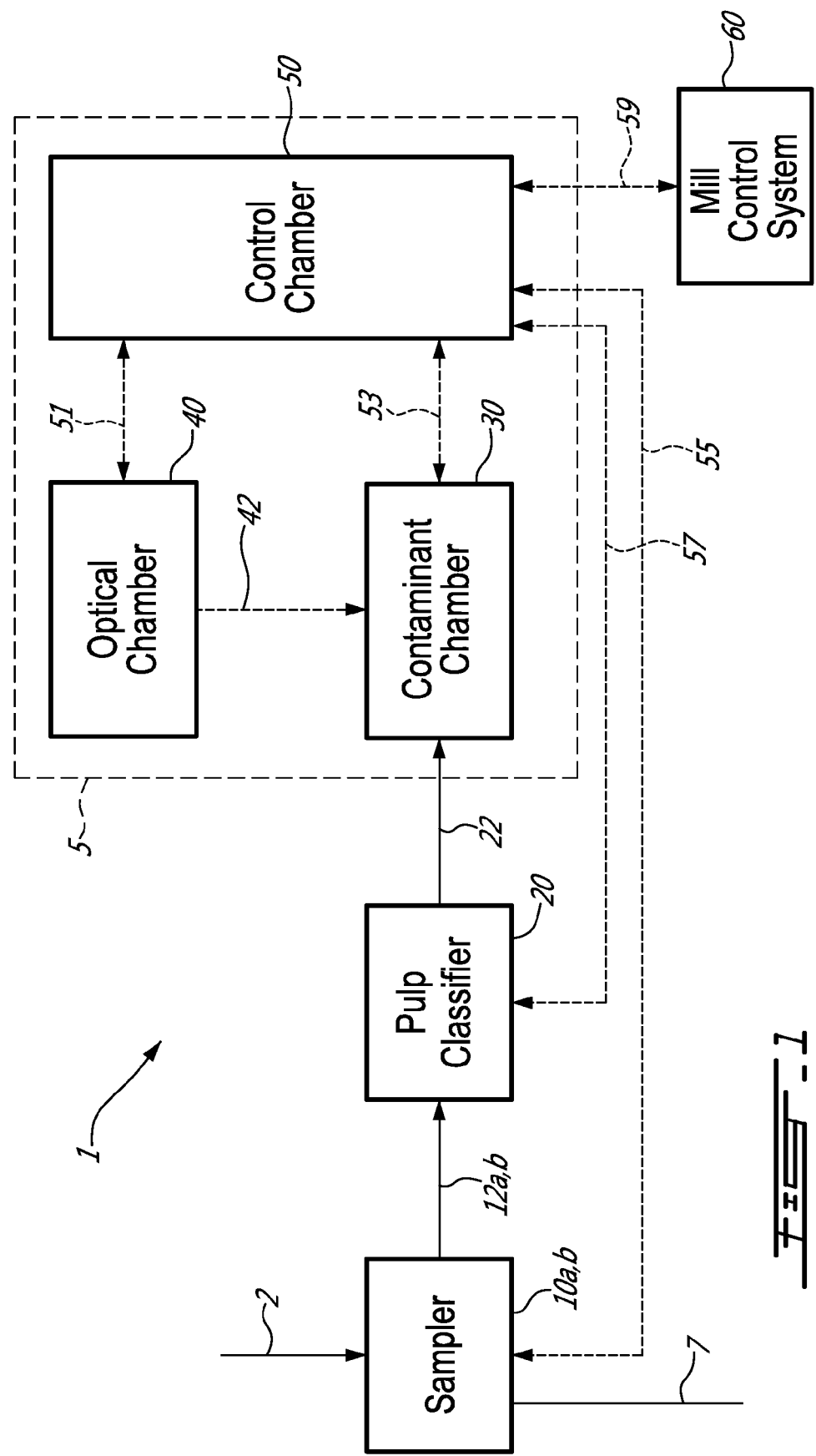
FIG. 1 is a schematic flowsheet of an on-line analyser of macrocontaminants according to one embodiment of the present invention.

Macrocontaminants are a minor component in an aqueous suspension whose principal components are long fibres and fine elements. Transport of the sample to the analyser can be done manually or automatically using commercially available pulp samplers.

In summary, the on-line automated analyser described identifies the type of macrocontaminants isolated from pulp or white water samples and measures their quantity, size and projected area by image analysis. In this unit, all actions are automated so that manual intervention is limited to calibration and maintenance procedures. In order to obtain a clear image for subsequent analysis, the macrocontaminants are first separated from the fibrous material and concentrated using a screening system with slot apertures of a 0.003" to 0.006". The analyser is designed to be either a stand-alone unit with an incorporated screening system or it can be retro-fitted to an existing commercial pulp classifier. Pulp or white water streams are added to the inlet of the pulp classifier either manually or via auto-sampler. After screening has removed virtually all the fibres, the isolated macrocontaminants dispersed in water are automatically discharged to a specially designed contaminant cell. In this cell, contaminants in water are first mixed uniformly by air jets after which the macrocontaminants separate according to their difference of density with water. Light-weight macrocontaminants such as waxes, low-density stickies, hotmelts, plastics, varnishes and combinations thereof float to the top of the cell whereas the contaminants denser than water settle to the bottom of the cell. Heavy-weight contaminants sink because they are more dense than water, and include macrostickies, shives, hotmelts, high-density plastics, varnishes, and black contaminants such as toner or dirt and combinations thereof. Lighting in the contaminant chamber and the material and color of the settling plate assure adequate visualization and discrimination of contaminants prior to image capture by cameras lenses focusing on the top of the water phase or at the bottom of the contaminant cell. Contaminant dispersion in the water phase of the chamber, image capture and image analysis are repeated to assure that the number of contaminants measured are sufficient enough to ensure statistical significance of the results. The data from all the images of the sample are averaged and a report is prepared that includes the total number and area of heavy- and light-weight contaminants. The report can be visualized on the computer screen of the analyser or sent to mill data base and control systems. Data is stored in the processor with a link to the original image of the contaminants. This data storage will also allow the user to view the historic trends of the total number and area of each contaminant type. In addition to the two categories of contaminants, heavy-weight contaminants can be further discriminated into four separate categories that include: 1. white or whitish macrostickies including hotmelts, plastics and varnishes; 2. shives; 3. black contaminants or dirt, such as toner; or, 4. plastics and varnishes. If the analyser is coupled to an agglomeration chamber, identification of agglomerated microstickies will also be possible. These features of the analyser and the method will be described in greater detail with reference to the drawings.

Referring to the drawings for greater detail, FIG. 1 illustrates the main components of an on-line automated analyser of macrocontaminants and its associated equipment 1. The on-line automated analyser of macrocontaminants 5, may be identified herein by the trademark FPAutoSpeck™. The analyser 5 counts macrocontaminants isolated from pulp or white water samples.

Though macrocontaminants 22 from a process stream 2 in question pertain principally to stickies, light-weight macrocontaminants and dirt in recycled pulps, the same on-line automated analyser 5 can be used for the identification and quantification of harmful components like shines in virgin pulps. The letter suffixes a and b after a reference number refer to manual and on-line samples respectively.

The on-line automated analyser 5 is housed in a stainless steel cabinet that has three separate compartments or chambers named according to their main function: Contaminant Chamber 30, Optical Chamber 40 and Control Chamber 50.

The cabinet serves uniquely to protect the electronic components from vibration and the hot, humid and harsh environment of a mill. As such, as long as the cabinet is rugged and waterproof, it can be composed of several materials such as plastic and metal. In this diagram, the on-line automated analyser 5 of macrocontaminants 22 is coupled to a commercial pulp classifier 20 and, for on-line analysis, commercial on-line samplers 10b can be added.

Pulp or white water samples 12a/b are fed via a sampler 10a/b that is either manual 10a or an on-line auto-sampler 10b to a pulp classifier 20 which separates the contaminants 22 and transfers them to the Contaminant Chamber 30. The Contaminant Chamber 30 serves to first separate or isolate contaminants 22 into either light-weight 31 or heavy-weight macrocontaminants 32 and then to disperse the contaminants prior to image capture 42. In a preferred embodiment, two cameras located in the Optical Chamber 40 take pictures (perform image captures) of either the light-weight 31 or heavy-weight contaminants 32. The light-weight contaminants 31 may include waxes, hotmelts, plastics and/or varnishes whereas the heavy-weight contaminants 32 may include macrostickies, shines, plastics, varnishes, hotmelts and/or black contaminants or dirt, such as toner.

The control chamber 50 has part of both the hardware and software to operate the components of the Optical and Contaminant Chambers of the FPAutoSpeck™ 51, 53 respectively, as well as the hardware and software for the autosamplers and pulp classifier 55, 57 respectively. The image analysis software then counts the number of light-weight 31 and heavy-weight contaminants 32 and measures their surface area. In addition to the total number and area of contaminants, a report is made in the form of a histogram that shows the number of the contaminants within a given size range or bin. The report can be visualized on the computer screen of the FPAutoSpeck™ or the data is sent 59 to mill data and control systems 60. Data is stored in the processor with a link with the original images of the contaminants. This data storage will also allow the user to view the historic trends of the total number and area of each contaminant type.

Figure 2:
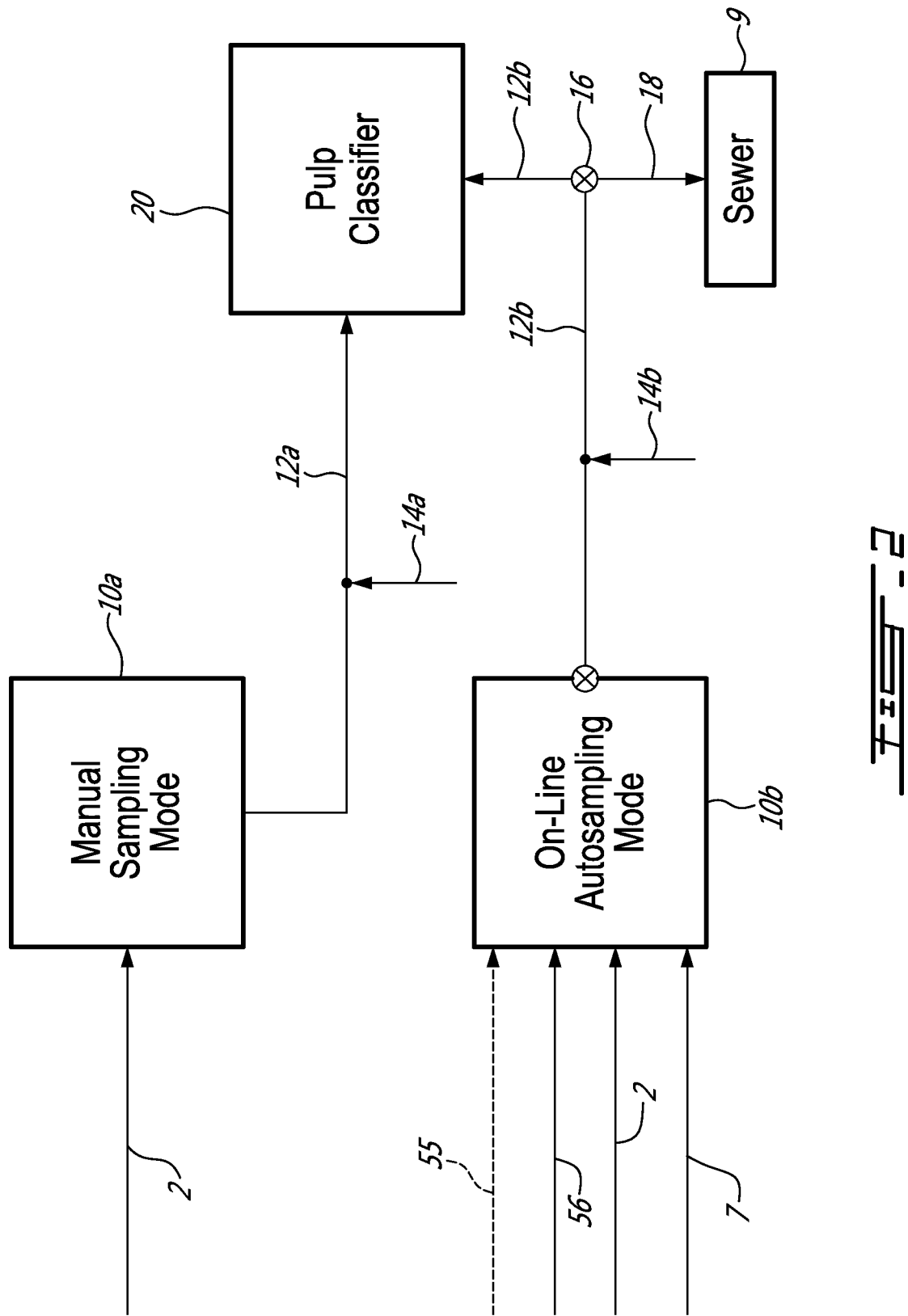
FIG. 2 is a flowsheet of another embodiment of an on-line analyser according to another embodiment of the present invention showing how a pulp and/or a white water sample are fed to a pulp classifier either manually or on-line via a low or medium consistency commercially available auto-sampler.

FIG. 2 shows how pulp or white water samples from a pulp or white water line are fed to a pulp classifier either manually or on-line via a low or medium consistency commercially available auto-sampler 10b.

For the manual sampling mode (a) process stream sample 2 of pulp or white water is taken by a manual sampler 10a. A fraction 12a of known volume and/or solids content are fed manually to a dilution loop or receiving vessel of the pulp classifier 20. Prior to treatment of the fraction, a manual mode of operation is chosen in the operating window of the software interface 14a. The manual sampling mode (a) requires that values on the sample volume or solids content be keyed into the program before adding a fraction of sample. After adding the fraction and pressing start in the window of the user interface 14a, the sample can be treated automatically.

For the on-line sampling mode (b), the auto-samplers 10b are controlled by one of the programmable logic controllers (PLCs) 64 of the on-line automated analyser 1 of macrocontaminants via electrical and/or electronic connections 55. The auto-sampler parameters and control can be accessed by the user through the window of the user interface 14b. Controllable hardware may include a sample piston or diaphragm and valves 56 for flow of air and sample. A sight glass window in the sample line allows the user to determine the amount of time it takes the sample to travel to the inlet of the pulp classifier. This time of travel and opening of the piston must be calibrated for each auto-sampler line. The constant pressure of the flushing water 7 serves to push the sample through the piping. A sample deviation valve 16 is then switched at a specified time to allow flow of the sample carrot to the inlet of the pulp classifier 20. The flow of flushing water 7 can alternatively deviate to the sewer 9 via a drain 18. In order to relate contaminant number to the pulp weight or white water volume, on-line sampling requires the transfer 59 of data on the volume or solids content of the sample and sometimes the pressure in the sample line from the mill data control system 60 to the processor of the on-line automated analyzer 5 of macrocontaminants. Alternatively, the pulp weight can be determined by measuring the consistency of the pulp sample making-up the carrot using an on-line consistency meter.

Figure 3:
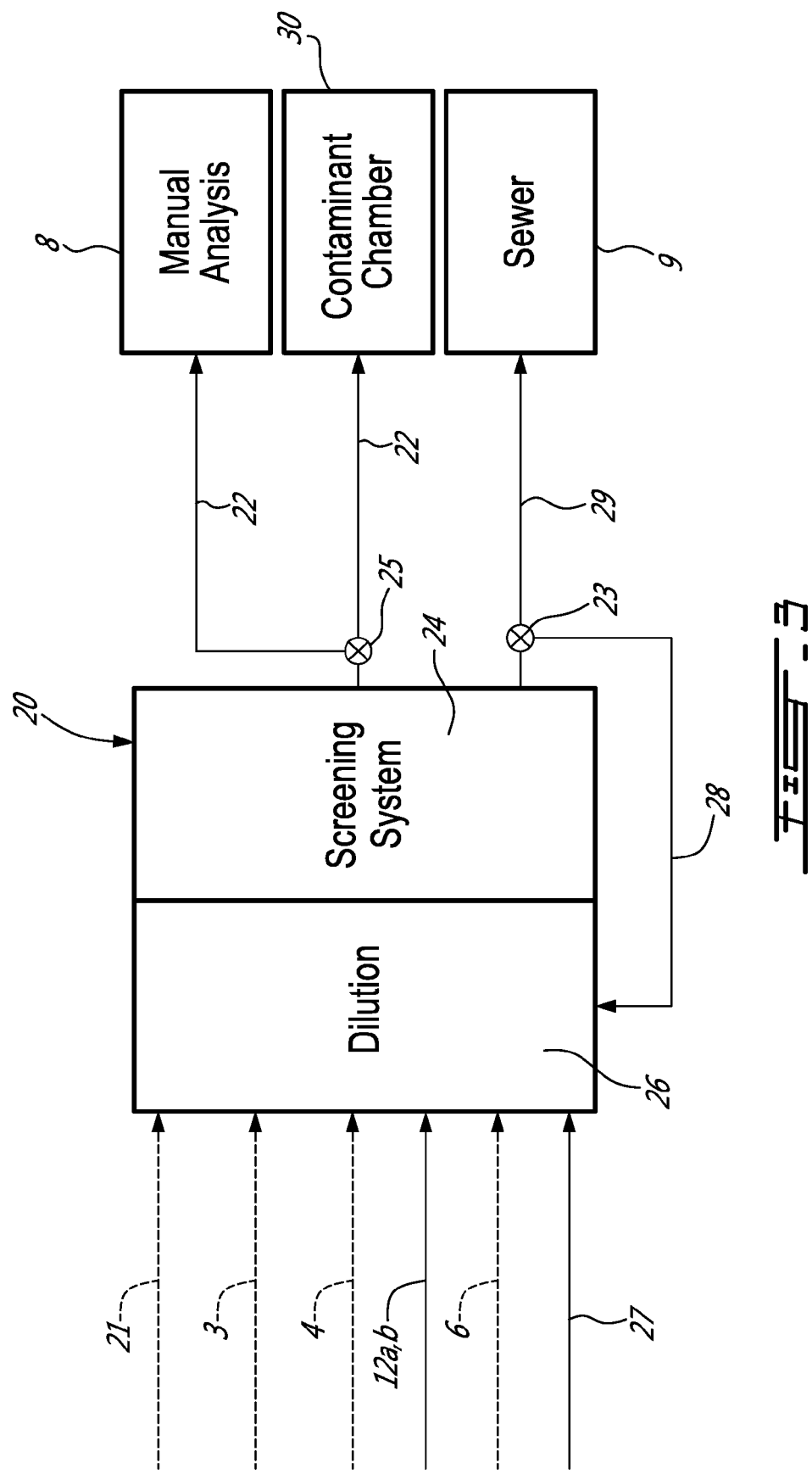
FIG. 3 is a schematic flowsheet of a pulp fractionator connected to the on-line analyser of FIG. 1, the pulp classifier serving to isolate a fraction of macrocontaminants from the pulp fibre stream, that may optionally be transferred to the on-line analyser according to another embodiment of the present invention for analysis of type, number and area.

In pulp streams 2, macrocontaminants are few in numbers and their identification by an image analysis system becomes difficult where the contaminants of interest represent the minor component in slurry. The pulp classifier 20 serves to isolate macrocontaminants 22 from the pulp fibre stream 2, where they can be subsequently transferred to the on-line automated analyser 5 of macrocontaminants 22 for analysis of type, number and area. FIG. 3 shows how the pulp classifier 20 is coupled to the FPAutoSpeck™. The FPAutoSpeck™ can be retrofitted to a commercial pulp classifier or any other custom pulp classifier such as contained within the analyser 1 of macrocontaminants. Alternatively, contaminants may be segregated and concentrated from pulp or white water through circulation through a screening system 24 that comprises a screen, pressure screen or hydrocyclone-type reverse or Uniflow cleaner. A deviation valve 23 will allow several passes or recirculation through the same unit or through a series of units to ensure that virtually all fibres and fine elements are removed to permit optimal visualization of the macrocontaminants. The same valve 23 will allow draining of rinse water or discarded fibres 29 to the sewer 9.

Pulp or white water samples 12a/b are fed either manually 12a or via an on-line auto-sampler 12b to the dilution loop 26 or reservoir of the pulp classifier 20 for dilution with contaminant-free water at 30° C. or less. After dilution, the sample is passed through a screen with slots of $\frac{1}{3000}^{th}$ to $\frac{1}{6000}^{th}$ of an inch in width which allows passage of fibres and small fibrous and non-fibrous elements while preventing passage of macrocontaminants 22 of greater or equal to 75 or 150 µm in width. Low slot velocities of less than 1 m/s will ensure adequate removal of the fibre while concentrating the macrocontaminants 22 on one side of the screen. At higher velocities, contaminant concentration and segregation can be achieved by several passes or recirculation 28 through the same screen. The concentrated macrocontaminants are then transferred to the contaminant cell 34 of the FPAutoSpeck™ analyser 5 for analysis or to a second site for manual analysis 8 of sample. Rinse water 27 is flushed through the screen to prevent clogging of the slots and to rinse the transfer lines of the macrocontaminants. The pulp classifier 20 is then ready to treat another sample while images of the macrocontaminants are captured for subsequent image analysis. Other connections to the pulp classifier 20 include water level sensors 21; electrical and electronic connections 3; valves and control sensors 4, and sample mixing 6 means.

Figure 4:
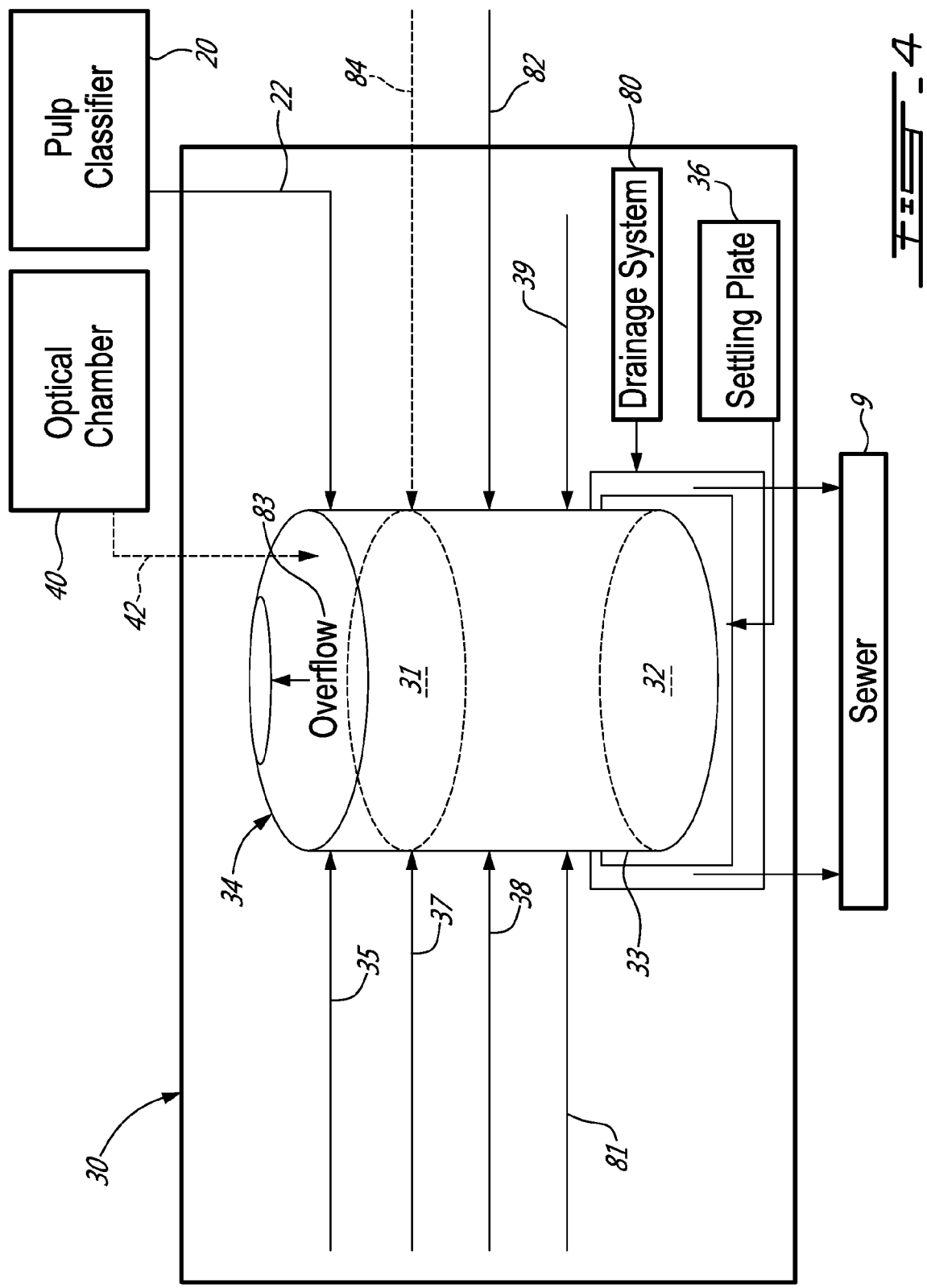
FIG. 4 is a schematic flowsheet of one embodiment of a contaminant chamber of the on-line analyser according to FIG. 1, receiving the macrocontaminants and permitting their dilution, dispersion, discrimination, image capture, and eventually their transfer to the sewer.

Isolated macrocontaminants 22 from the pulp classifier 20 are transferred to the contaminant cell 34 of the Contaminant Chamber 30 as seen in FIG. 4. The Contaminant Chamber 30 keeps all liquid-handling components separate from the electronic parts of the FPAutoSpeck™. The chamber 30 serves to receive the macrocontaminants and permits their dilution, dispersion, discrimination, image capture, and eventually their transfer to the sewer 9. The Contaminant Chamber 30 is equipped with several components that include a contaminant cell 34, a retractable shower system 35 for sample dilution and rinsing, a settling plate 36, lights 37, air nozzles 81, pneumatic valves 38, water level sensors 39, water lines 82 (valves) and an overflow groove and funnel.

A main component enclosed within the contaminant chamber 30 is a contaminant cell 34. The contaminant cell 34 has a transparent base or contaminant settling plate 36 at the bottom of the cell. In a preferred embodiment the contaminant cell 34 includes a clear cylindrical cell 33 equipped with the contaminant settling plate 36. The cell may be arranged with a clear settling baseplate and an adjacent coloured background plate outside the cell. The various possible plates allow visualization of the contaminants and their adequate discrimination or determination of type. The cylinder 33 and plate 36 can be made of several clear materials such as glass, plexiglass or polycarbonate. The settling plate 36 can also be made of different coloured materials such as plastic, metal (untreated, anodized or electroplated) or tempered glass with a coloured background. In order to optimize visualization and discrimination of a given contaminant, the material used to construct the plate 36 can vary as well as its color. Settling plate 36 inserts are readily changed as needed for maintenance or for viewing of different contaminant types. A retractable shower system 35 permits either dilution of the sample or rinsing of the contaminant cell between samples. Pneumatic valves 38 control shower cover movement over the contaminant cell 34 or away to the side. A shower nozzle of the shower system 35 is fitted to a shower cover to prevent water spray onto the optical chamber window. The shower cover is retracted to permit image capture of the contaminants. The water volume is adjusted according to a predetermined level that allows adequate separation of light-weight and heavy-weight contaminants while allowing the objects to be at the focal length of the lens of the two cameras for optimal viewing and discrimination during image capture 42. Water level sensors 39 allow detection and control of the water level in the contaminant cell. Light-weight contaminants 31 will float whereas heavy-weight contaminants 32 will settle to the bottom of the chamber. Two series of air nozzles 81 and valves 38 permit dispersion of the contaminants between individual image capture by charged coupled device (CCD) such as a scanner, high definition camera 41/43 or video camera. For image analysis 70, two waterproof light emitting diode (LED) lights 37 equipped with wide angle lens are positioned to illuminate contaminants through the cylinder wall. Alternately, lights 37 can vary in number and be of various sources such as filament, laser or a gas discharge arc lamp. Lens, diffusers or filters can be added to provide lighting that illuminates contaminants without reflections or shadows. The functions described above associated with image transfer generally operate via electronic and electrical links 84. Repeat images are taken to assure statistical measurement of the macrocontaminants. Once the image capture 42 is completed, the cylindrical cell 33 is raised by two pneumatic valves 38 seated on the exterior walls of the cylinder. Note, pneumatic valves are of different types depending on their use. A rinse water valve is then activated and the shower 35 rinses the contaminant cell 34 free of contaminants. Rinse water 82 and macrocontaminants 31/32 are drained to the sewer 9 through the retractable base support plate by a drainage system 80. The drainage system 80 includes the drainage cylinder and the necessary piping. In case of accidental overflow of the contaminant cell 34, an overflow 83 groove and funnel is located at the back of the internal cylinder 33. A rubber seal located in the cylinder wall base assures a watertight seal between the cylindrical cell 33 and the settling plate 36. The cylindrical cell 33 is seated on the settling plate 36 insert fitted into a base support plate (not shown) made of stainless steel or other materials. This base plate is fixed on a retractable base plate drawer support facilitating maintenance and changing of contaminant settling plates 36.

Figure 5:
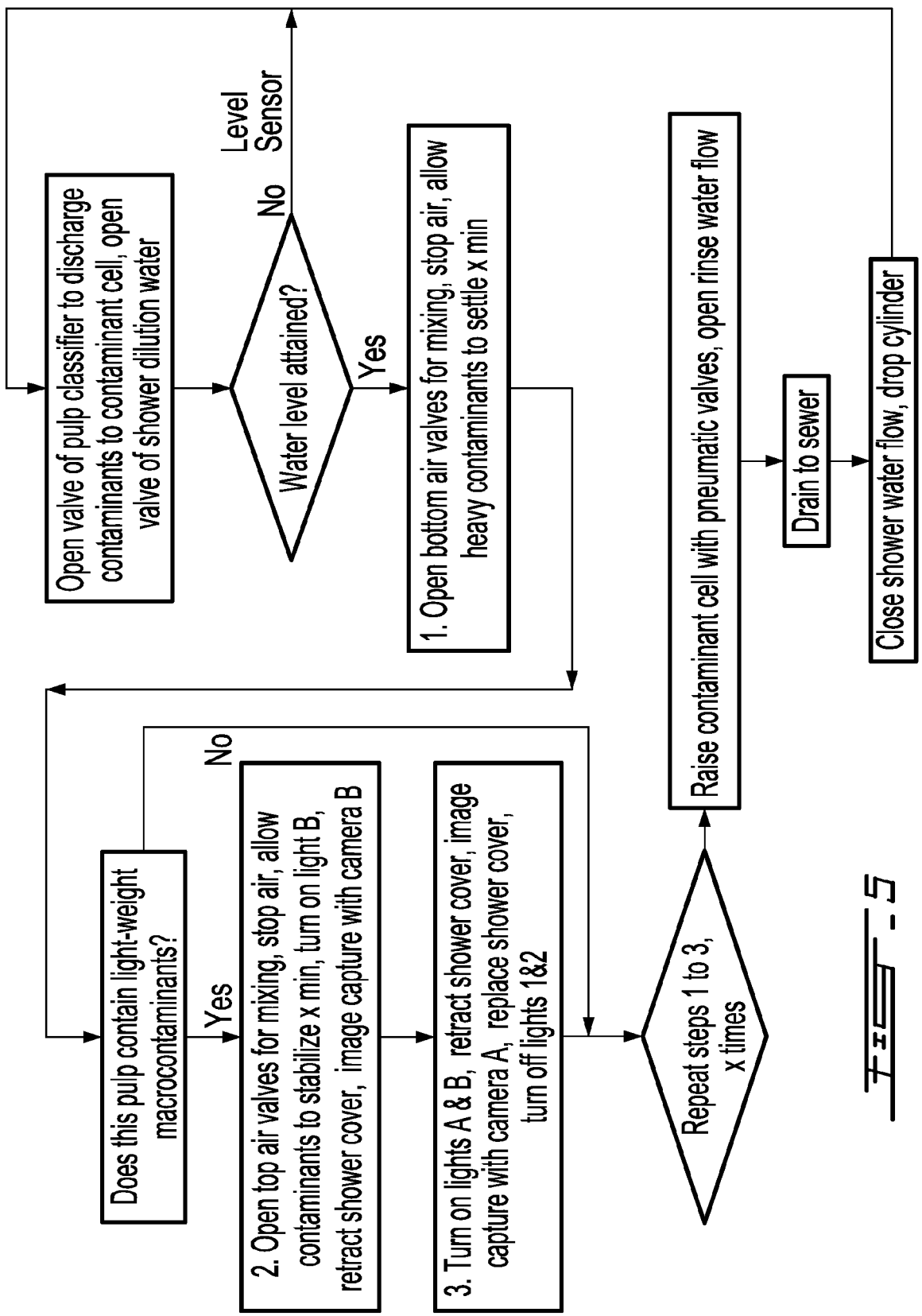
FIG. 5 is a logic diagram depicting a sequence of events that permit image capture and analysis of both light- and heavy-weight contaminants in a Contaminant Chamber according to one embodiment of the present invention.

The contaminant chamber 30 contains a series of hardware components that are synchronized to permit adequate image capture and analysis of both light-weight 31 and heavy-weight contaminants 32. FIG. 5 shows the necessary sequence of events.

Isolated contaminants are transferred to the contaminant cell 34 of the FPAutoSpeck™ when the pulp classifier valve 25 is opened discharging macrocontaminants to the contaminant cell 34. The water flow 82 (from the shower system 35) or for sample dilution is triggered at the same time. When the level sensors 39 indicate that the water level is attained, the shower water flow 82 is stopped and the contaminants are mixed for a pre-determined time with air injected from nozzles 81 located at the base and at the upper water level of the contaminant cell 34. After mixing, the air flow is stopped and the contaminants are allowed to settle for a pre-set time (x min) onto the contaminant settling plate 36. Because light-weight contaminants 31 are only present in certain types of recycled pulp or pulp waters, such as that made from old corrugated cartons, one of two image capture modes can be used.

If light-weight macrocontaminants 31 are present, air is injected for a pre-determined time through nozzles located in upper level of the cylindrical cell 33 just over the top water level. When the air flow is stopped, the contaminants are then allowed to stabilize. Light B 37 is then opened and the shower cover 35 is retracted to the side of the cylindrical cell 33 allowing image capture 42 with Camera B 43 through the optical window 44. Prior to image capture 42 of the heavy-weight or settled contaminants 32, Light A 37 is opened and Camera A 41 is then activated. After image capture 42, the shower cover 35 is replaced over the cylinder 33 of the contaminant cell 34 and Lights A 37 and B 37 are closed. This routine of Steps 1-3 is repeated until a pre-determined number of images are taken to allow analysis 70 with a statistically significant number of contaminants.

If light-weight contaminants 32 are not to be measured, Camera B 43 is not required and the Step 2 (mixing of light weight contaminants 31 and image capture 42) is omitted in the routine of steps from 1 to 3. Once the pre-scheduled number of images has been taken and the retractable shower system 35 is replaced in position over the contaminant cell 34, the contaminant cell cylinder 33 is raised by the pneumatically-controlled valves 38 and the contaminants are flushed to the sewer 9. The rinse water valve supplying water 82 to the retractable shower system 35 is activated to allow cleaning of the contaminant cell 34. After cleaning, the rinse water flow valve is shut and the contaminant cell cylinder 33 dropped shut. The FPAutoSpeck™ is now ready for reception of another sample of macrocontaminants 22.

Figure 6:
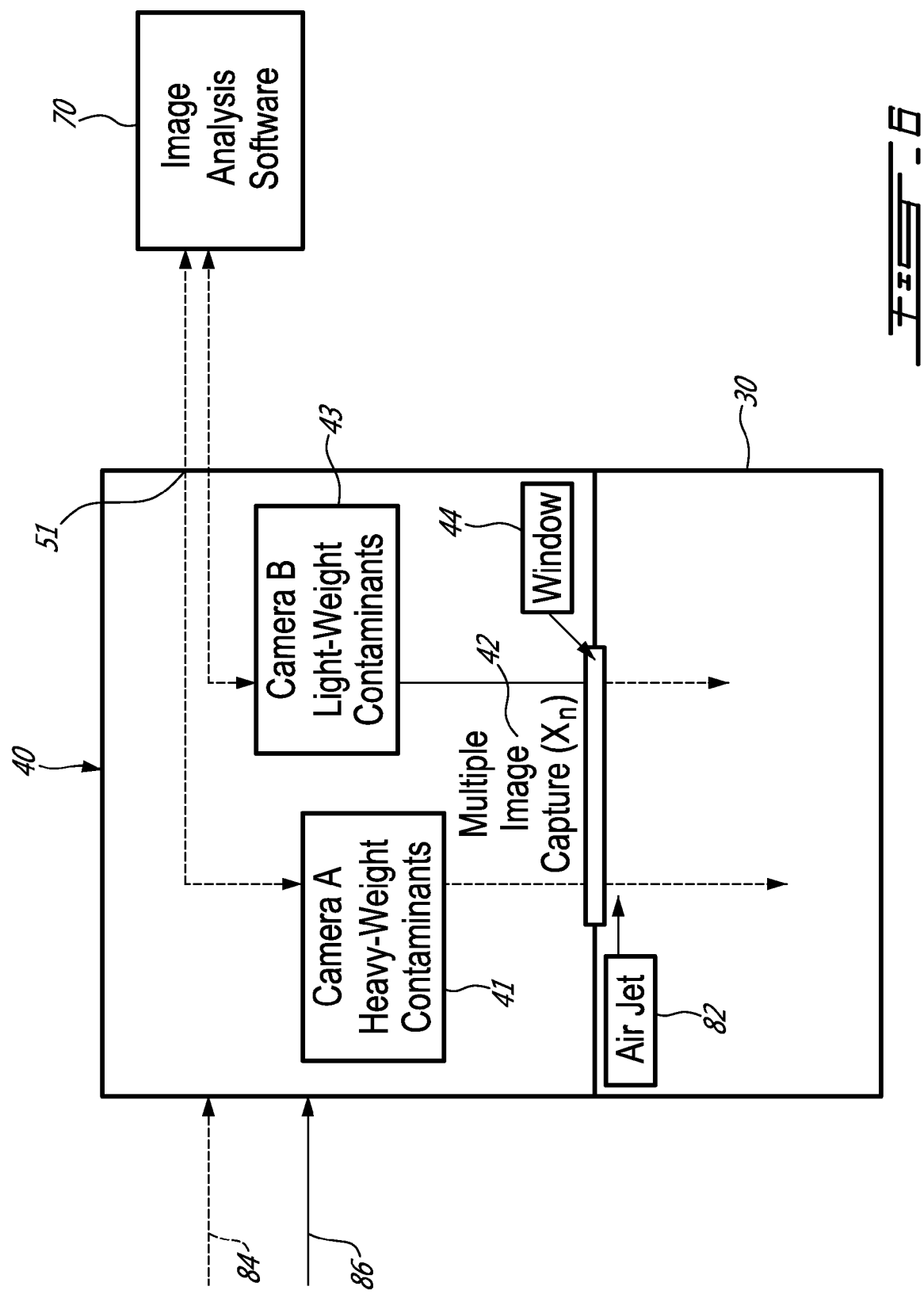
FIG. 6 is a schematic flowsheet of components of an optical chamber comprising digital cameras for image capture according to one embodiment of the present invention.

FIG. 6: Block Diagram of the Optical Chamber

The optical chamber 40 is a waterproof chamber containing one or more industrial-grade high definition digital cameras of at least 11 megapixels. Alternatively, industrial-grade scanners or high definition digital cameras or video cameras can be used. To keep cameras 41/43 and the processor cool, air flow valves 86 are opened to allow a flow of air inside both the Optical and Control Chamber (40/50 respectively).

The distances of camera A 41 and B 43 are set to clearly focus on either the heavy-weight contaminants 32 settled onto the contaminant settling plate 36 or the light-weight contaminants 31 floating on top of the water. Industrial lenses are used in combination with the cameras with focal lengths of 105 and 80 mm that allow visualization of contaminants. Lenses and extensions can be altered as needed. An optical window 44 protects the optical equipment from the water spray and wet environment of the contaminant chamber 30. Jets of air 82 under the window prevent water droplet formation on the optical window. The cameras are controlled by the computer 58 and camera interface software 70 located in the Computer Chamber 50. Image capture 42 is triggered by sequences of events in the contaminant chamber schedule (FIG. 5). Repeat images are taken after sample dispersion with air until statistical significance on the number of contaminants is reached. The captured images are then analyzed by the image analysis software 70.

Figure 7:
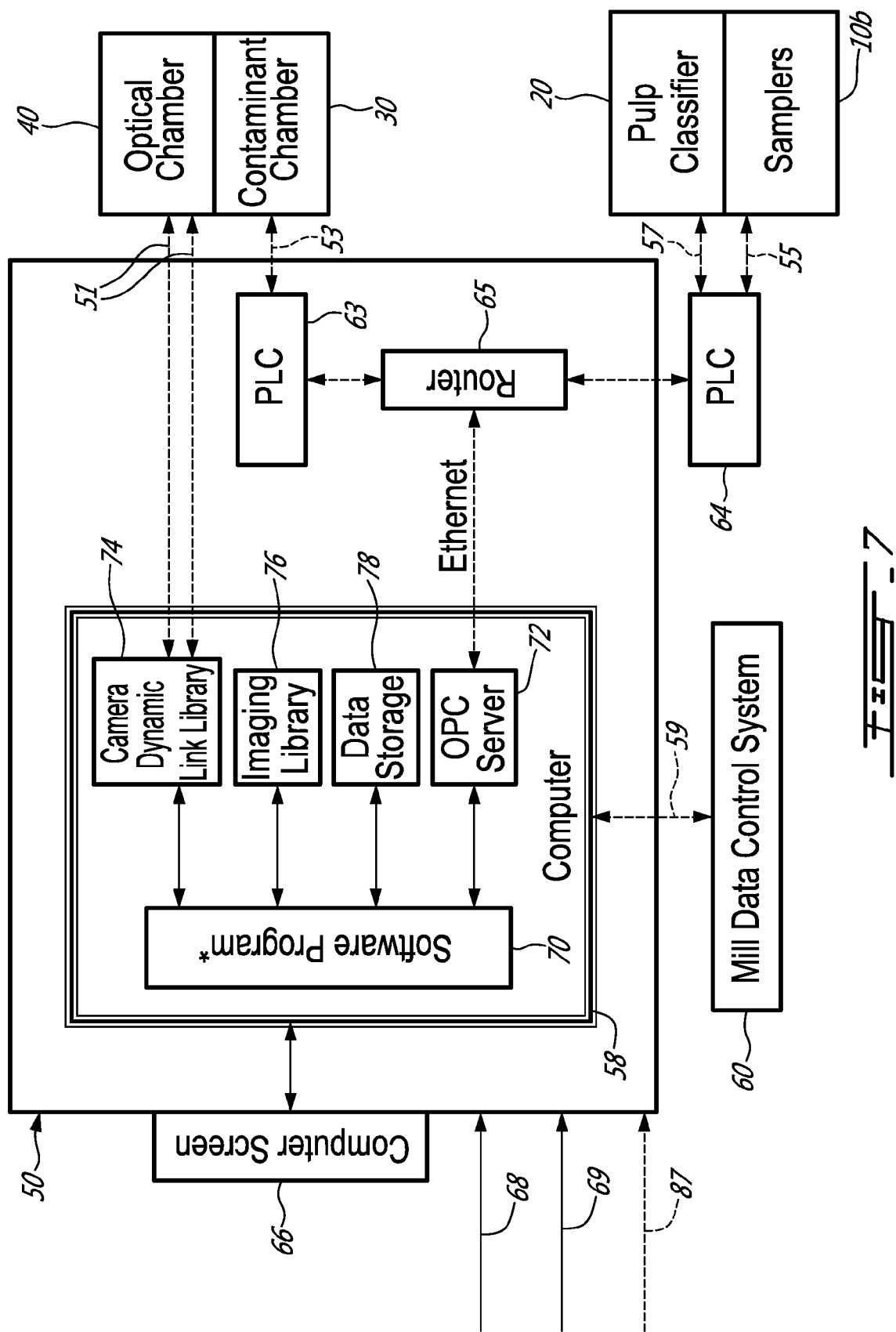
FIG. 7 is a schematic flowsheet of hardware and software components of a control chamber according to one embodiment of the present invention; these components perform specific tasks of the analyser, and comprise: communication to other units of the on-line analyser, such as the pulp classifier, auto-samplers, and cameras in the optical chamber, various valves and sensors located in the Contaminant Chamber, Programmable Logic Controller (PLC) hardware, router, computer screen, and links to the mill data control system.

FIG. 7: Block Diagram of Control Chamber and Communication

To achieve the detection of contaminants, FPAutoSpeck™ requires a series of hardware and software components which perform specific tasks. FIG. 7 shows a diagram of the Control Chamber 50, its electrical connections 87, and its communication to other units of the FPAutoSpeck™ such as the pulp classifier 20, auto-samplers 10b, cameras 41/43 in the Optical Chamber 40, various valves and sensors located in the Contaminant Chamber 30, Programmable Logic Controller 63/64 hardware, router 65, computer screen 66, and links 59 to the mill data control system 60. A computer Control Chamber 50 itself is a waterproof box that houses the hardware and software necessary to operate the FPAutoSpeck™. The temperature and humidity of the control chamber 50 are controlled by temperature sensor 69 that in turn regulates a vortex 69. Alternatively, other forms of air cooling 68 systems could be used.

Hardware Components:

An industrial-grade personal computer (PC) 58 is at the center of the Control Chamber 50 and the FPAutoSpeck™ on-line analyser 1. The main use of the PC 58 is to run the specialized software program 70, Macrostickies.exe, which supervises the execution of all the tasks required by the system. A Camera Dynamic Link Library 74, specific to the imaging device is installed on the PC as is, an Imaging Library 76 and OPC Server 72.

The PC 58 communicates to and from the two PLCs 63/64 through a router 65 that follows the Ethernet protocol. One PLC 63 handles the operations of the Contaminant Chamber while the other PLC 64 handles the operations of the Pulp Classifier 20 and Auto-samplers 10b. These PLCs 63/64 are used to implement logical sequences of actions and respond to events occurring to the devices to which they are attached. For the auto-sampler 10b, the PLC 64 operates from a user-defined schedule that decides which auto-sampler 10b is going to be active and then triggers the pulp sampling routine. When the pulp arrives to the Pulp Classifier 20, the PLC 64 monitors the screening operation and when complete, it opens a valve to transfer the isolated contaminants 22 to the Contaminant Cell 34. Once the discharge sequence of the contaminants is complete, the PLC 64 forces a washing of the Pulp Classifier 20 to make it ready for the next pulp sample. Once the contaminants 22 arrive in the contaminant cell 34, the Contaminant Chamber PLC 63 activates a routine of steps as indicated in FIG. 5. As shown in the diagram, the PLC 63 controls the valves for air and water flow 82, pneumatic valves 38 for retracting the shower cover 35 and raising the contaminant cell cylinder 33, opening and closing of the lights 37, and initiating the cleaning cycle. Through a OPC server 72, the PLC 63 also signals to the PC 58 when it is time to take the pictures of the contaminants. The two high-resolution cameras 41/43 are connected to the PC 58 by separate USB (Universal Serial Bus) connections that provide bi-directional communications between the cameras 41/43 and the PC 58.

The PC 58 also physically houses the hard disk 78 that stores the historical records of the analyses. The numerical values of the records are stored in a database, such as an Access™ database, and the images are stored in a standard format at a separate location on the hard disk. A touch-sensitive Computer Screen 66 allows interaction between the user and the FPAutoSpeck™ software and allows visualization of the image analysis results. Normally, the FPAutoSpeck™ system has no keyboard or mouse. Touching the screen replicates the action of a mouse so that the user can select specific pages of Macrostickies.exe to be displayed. If data needs to be entered, an on-screen keyboard appears which allows the user to enter data. Note other external devices such as a keyboard can be added and used via external ports such as a USB port.

Software Components:

There are four important software components of the FPAutoSpeck™ analyser. The custom software program 70 called Macrostickies.exe was developed in VB.Net but could be written in C++ or any other programming language. The software 70 coordinates and controls the behaviour of the hardware components, displays the analysis results and reacts to the user interactions. The Camera Dynamic Link Library 74 is a bi-directional interface between Macrostickies.exe and the cameras 41/43. In one direction, the library passes the image resolution, optical gain, and live image preview and snapshot requests to the cameras 41/43. In the other direction, it passes the actual digital images to Macrostickies.exe. The third component is an Imaging Library 76 which provides the necessary image processing routines to correctly locate and measure the specks of contaminants on the images. The last component is an OPC server 72 (Object linking and embedding for Process Control) that provides bi-directional communications between the PLCs 63/64 and Macrostickies.exe.

Macrostickies.exe is the master program 70 of the FPAutoSpeck™ system. It coordinates the different tasks of the system through an array of software and hardware links to the system's various components. A high-level computer programming language, VB.Net™, with a large number of general purpose functions and features allowed for the development of the powerful Macrostickies.exe program. However, in the development of applications, VB.Net™ requires access to special hardware such as digital cameras and PLCs. This access is provided through the addition of special extensions and software gateways which come in the form of specially packaged libraries. The FPAutoSpeck™ application requires a number of such libraries.

The Camera Dynamic Link Library 74 provides access to the cameras 41/43. The library serves as a bi-directional conduit to the camera hardware. Through it, Macrostickies.exe can enable and disable the cameras, read or write the camera parameters, turn on or off live image preview and trigger the acquisition 42 of snapshots.

The Imaging Library 76 is also a dynamic link library containing standard image processing functions or filters. One possible source is a public domain library available by AForge. The detection of contaminants is determined by running the images 90 acquired by Macrostickies.exe through a sequence of a subset of these filters. Typically, Macrostickies.exe will call a filter by passing the image to be processed along with some filter-specific parameters. The filter then returns a modified image.

Currently the macrocontaminant analyser uses an OPC Server 72 as another type of specialized library. It serves as a protocol for communicating with field instruments. "Object Linking and Embedding" is a Microsoft technology which enables the communication of information between applications but any other type of custom or commercially available communication's protocol specific for field instruments would be suitable. In this particular case, the OPC 72 communicates with the variables of the two PLCs 63/64. An example of this occurs when the status of a valve changes, the PLC immediately communicates this information to the OPC Server 72. In turn, the OPC Server 72 interrupts Macrostickies.exe to let it know of the change. In the other direction, Macrostickies.exe can initiate the acquisition and screening of a pulp sample 2 by requesting a specific variable of the OPC Server 72 to be turned on. The OPC Server 72 responds by passing this request to the PLC 64 attached to the Pulp Classifier 20.

Figure 8:
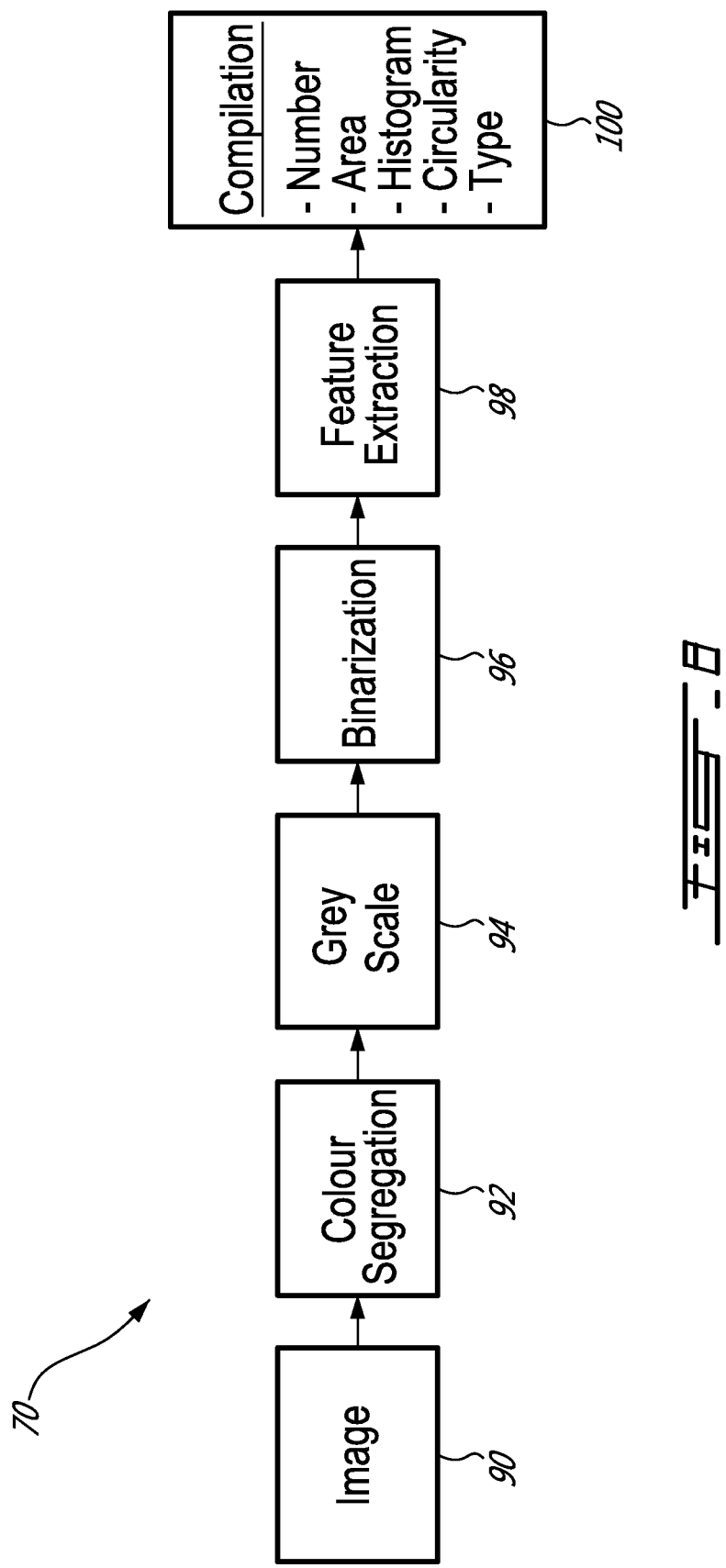
FIG. 8 is a schematic flowsheet of parameters of an image analysis program, treating images captured by the cameras and determining the type, number and size of the macrocontaminants of one embodiment of an on-line analyser according to FIG. 1.

FIG. 8: Block Diagram of Image Analysis Parameters

The image analysis software 70 is one of the key components of the FPAutoSpeck™. It serves to treat images captured by the cameras and determine the number and size of the macrocontaminants 22. FIG. 8 shows the main parameters of image analysis.

Once an image 90 is captured by the cameras 41/43, it is analyzed by the imaging software 70 for contaminant identification, size measurement and number. Initially, light-weight 31 and heavy-weight contaminants 32 are imaged by separate cameras 41/43. Once these images 90 are acquired, the images are processed by Macrostickies.exe to enhance detection, identification, area measurement and enumeration. The first treatment often includes color segregation 92. Often the red, green and blue (RGB) channels are used for filtering. Alternatively, the hue, saturation, and luminance (HSL) can be used. In some cases, an additional segregation based on brightness or gamma may also be included. Following color segregation, the images are converted to a grey scale image 94. A threshold in grey level detection or binarization 96 is then applied before analysis of the image. The extraction of features 98 such as the particle area, circularity and number of particles within a given size range are extracted and then sent for data compilation 100. The software then counts the number and area of each type of contaminant and creates a histogram of the contaminants within a given size range or bin. The report can be visualized on the computer screen 66 of the FPAutoSpeck™ or sent to mill data and control systems 60. Data is stored in the processor 78 to show images of the contaminants or to view the historic trends of their total number and area.

Figure 9:
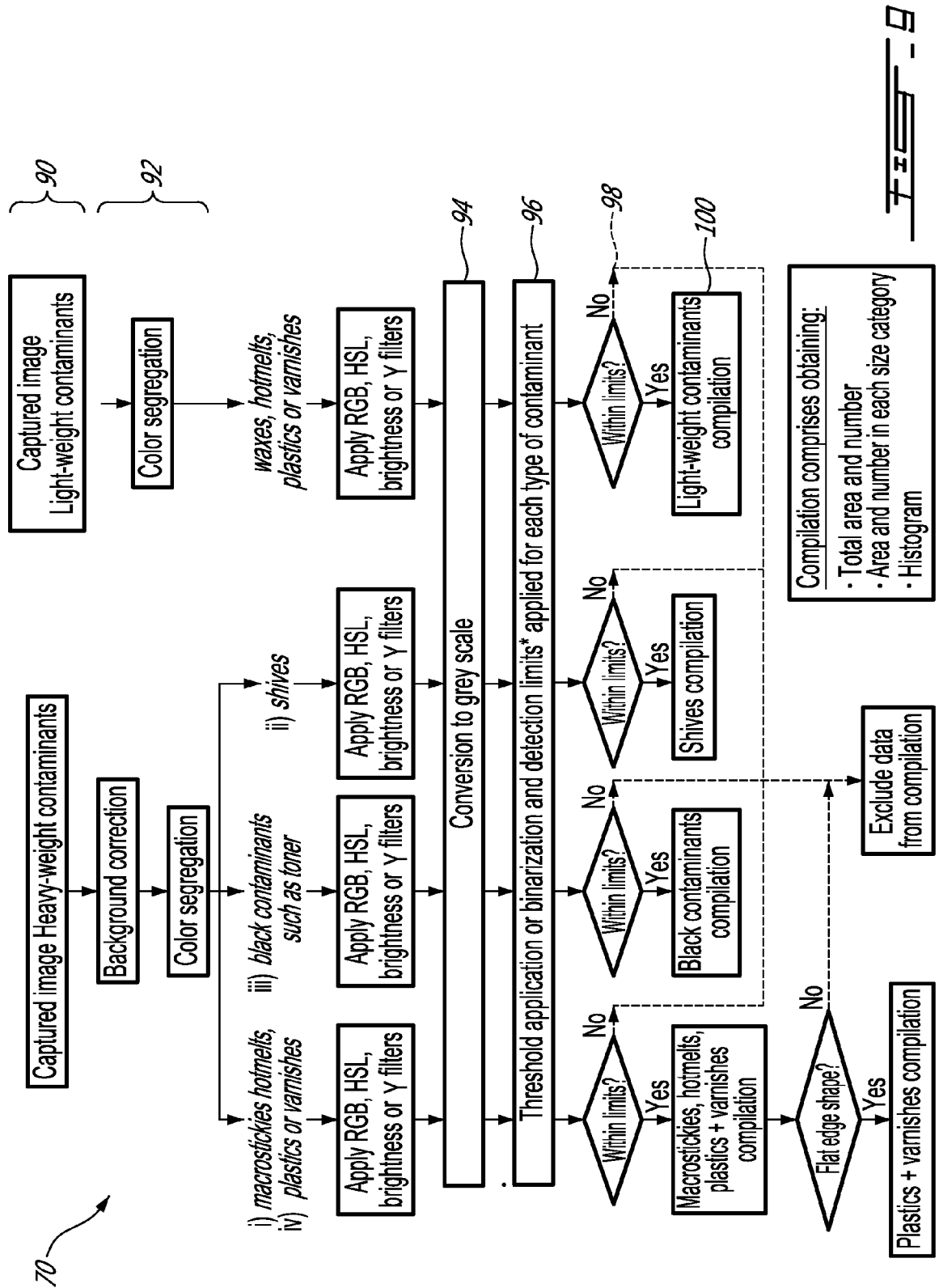
FIG. 9 is a logic flow diagram illustrating further details of the steps used to identify and characterize light- and heavy-weight macrocontaminants of the on-line analyser according to FIG. 1.

FIG. 9: Details of Image Analysis

FIG. 9 shows further details of the steps used to identify and characterize light- and heavy-weight macrocontaminants 31/32. The right side of the schema shows how the image analysis software analyzes light-weight contaminants 31. Light-weight contaminants 31, such as waxes, low density stickies, hotmelts, plastics and varnishes, are those of density smaller than water which floated on the top of the water in the contaminant cell 34. Images of these light-weight contaminants 31 are imaged separately by a camera 43 focused on the water surface. The image is first treated to segregate the colors 92 and enhance feature detection 98. Image treatment with RGB (red, green, blue) or HSL (hue, saturation, luminance) filters can be performed. Brightness, contrast and gamma 92 can enhance visualization of the light-weight contaminants 31. Other image manipulations such as inversions can also be performed. After conversion to a grey level 94, a specified threshold 96 is applied for the light-weight contaminants 31 as well as a particle size detection limit. To eliminate the detection of fibres, shives, air bubbles or small artifacts, a detection limit is also applied. Detection limit are specified by the particle maximum width or estimated diameter. Particles within the specified range of the detection limit are measured and enumerated whereas those outside of the specified range are excluded from the compilation 100.

Heavy-weight macrocontaminants 32 are those of density greater than that of water which settled on the insert of the contaminant cell 34 and were imaged by a second camera 41 and the image 90 acquired by the image analysis software 70. The image analysis software 70 of the FPAutoSpeck™ allows further contaminant identification of the heavy-weight macrocontaminants 32 into the following four different categories: i) white or whitish macrostickies, plastics, varnishes and/or hotmelts; ii) shives; iii) black contaminants or dirt, such as toner or iv) plastics and/or varnishes. If the FPAutoSpeck™ is coupled to an agglomeration chamber that brings small contaminants in a size range where they can be screenable, identification of agglomerated microstickies is facilitated. The i) white or whitish heavy-weight macrocontaminants are examined in a similar sequence as the light-weight contaminants 31. One exception is that the background is corrected to assure an image without halos. The other exception is that the filtering and image enhancement parameters are different than those used for the light-weight contaminants 31. The detection limits are the same but the threshold limit 96 is different. The area of particles with maximum widths within the detection limit are measured and counted and compiled 100 into a report. At this point, the white macrocontaminants counted include any plastics or varnishes included in the sample. For the identification of plastics and/or varnishes, the image analysis software will count those objects.

As for plastics and varnishes, the exact parameters for shives and black contaminants or dirt, such as toner have been determined. A proposed schema for identification of the black contaminants or dirt and shives is described. Again image filters and enhancements are applied to optimize the image. Different detection limits also facilitate identification of the shives. For shives, plastics and varnishes, detection limits also include other properties such as size and shape.

FIG. 10: Block Diagram of Data Storage

FIG. 10 shows how analysed images 90 are converted to numerical data 100, graphs 104, data tables 105, or stored 78 as an image file 107 (some examples include emf, wmf, jpg, jpeg, jfif, jpe, png, tiff, among others). An image 90 is analysed 70 as shown in FIG. 9. The numerical data 100 is presented in both chart 104 and data table 105 format on the screen of the FPAutoSpeck™. Alternately, numerical data 100 can be transferred to the mill data system 60 via Ethernet wiring or by wireless connection. Data 100 is also stored on the hard drive 107 of the PC 58 with a linked to the images from which they were measured. The linked data and picture 108 can be transferred to a USB key or printed 109.

REFERENCES

1. Doshi, M. R., De Jong, R. L. and Aziz, S. Method of measuring macro and micro stickies in a recycled sample containing pulp fibers. United States patent US20080283206A1 (November 2008).
2. Castro, C. and Dorris, G. M. Measuring microstickies deposition by monitoring pressure drop through a collector. *Progr. Pap. Recyc.*, 13(3):23-33 (2004).
3. Sitholé, B. and Filion, D. Assessment of methods for the measurement of macrostickies in recycled pulps. *Progr. Pap. Recyc.*, 17(2):16-25 (2008).
4. Tappi. Macro stickies content in pulp: the pick-up method (1999).
5. Doshi, M. R. A review of stickies measurement methods. *Progr. Pap. Recyc.*, 18(3):21-32 (2009).
6. Di Cesare, N. Method for measuring hydrophobic contaminants in paper pulp. United States patent US20080308241 A1 (December 2008).
7. Horn, D., Lueddecke, E., Gierulski, A., Kroehl, T. and Lorencak, P. Method for determining resin particles in paper stocks. U.S. Pat. No. 5,486,904A (January 1996).
8. Esser, A., Runge, F. and Kaub, H.-P. Method and apparatus for determining the size distribution of different types of particles in a sample. U.S. Pat. No. 5,940,177A (August 1999).
9. Carr, W. F. System for monitoring contaminants with a detector in a paper pulp stream. U.S. Pat. No. 4,758,308 (July 1988).
10. Banerjee, S. Method for sensing stickies. U.S. Pat. No. 6,841,390B1 (Janurary 2005).
11. Dorris, G. and Castro, C., Automation of a microstickies deposition tester relating the rate of deposition to the pressure drop across a collector, Presented at the 94$^{th}$ PAPTAC Annual Meeting, Montreal, February 5-7. p. (2008).
12. Monte, M. C., Blanco, A., Negro, C. and Tijero, J. Development of a methodology to predict sticky deposits due to the destabilisation of dissolved and colloidal material in papermaking—application to different systems. *Chemical Engineering Journal*, 105:21-29 (2004).
13. Pelton, R. and Lawrence, D. A new laboratory approach for evaluating kraft mill pitch deposit control additives. *J. Pulp Pap. Sci.*, 17(3):J80-J84 (1991).
14. Sitholé, B., Filion, D. and Allen, L. H. A laboratory test to measure deposition in recycled paper making. *Paper Technology*, 40(1):26-30 (1999).
15. Meric, J.-P. Process and apparatus for counting biological particles. U.S. Pat. No. 3,830,569 (August 1974).
16. Weinberger, S. R. and Hlousek, L. Apparatus for microfluidic processing and reading of biochip arrays. U.S. Pat. No. 7,046,357B2 (May 2006).
17. Basiji, D. A. and Ortyn, W. E. Imaging and analyzing parameters of small moving objects such as cells. U.S. Pat. No. 6,473,176B2 (October 2002).
18. Cabuz, C. and Cabuz, E. Flow control system of a cartridge. U.S. Pat. No. 7,420,659B1 (September 2008).
19. Cabuz, C., Cabuz, E. and Zook, D. J. Miniaturized flow controller with closed loop regulation. U.S. Pat. No. 7,061,595B2 (June 2006).
20. Dertinger, S. D. Method for the enumeration of micronucleated erythrocyte populations while distinguishing platelets and/or platelet-associated aggregates. U.S. Pat. No. 7,425,421B2 (September 2008).
21. Fukuda, M., Nakamoto, H., Seshimo, H. and Tohori, H. Optical particle analyzing apparatus having two types of light source. U.S. Pat. No. 5,260,764 (November 1993).
22. Gershman, R. J., Hansen, W. P., Hochberg, A. M. and Garland O'connell, J. Automated detection of platelets and reticulocytes in whole blood. U.S. Pat. No. 4,325,706 (April 1982).
23. Gu, Y. and Padmanabhan, A. Assay implementation in a microfluidic format. U.S. Pat. No. 7,553,453B2 (June 2009).
24. Inoue, T. Method of demarcating two-dimensional distribution. U.S. Pat. No. 5,006,986 (April 1991).
25. Kubota, F. and Kusuzawa, H. Particle analyser. U.S. Pat. No. 5,831,723 (November 1998).
26. Mueth, D., Plewa, J., Shireman, J., Anderson, A., Gruber, L. and Rosenbaum, N. H. Multiple laminar flow-based particle and cellular separation with laser steering. U.S. Pat. No. 7,402,131B2 (July 2008).

27. Ortyn, W. E., Basiji, D. A., Morrissey, P., George, T., Hall, B., Zimmerman, C. and Perry, D. Blood and cell analysis using an imaging flow cytometer. U.S. Pat. No. 7,522,758B2 (March 2009).
28. Padmanabhan, A. and Fritz, B. S. Miniaturized cytometer for detecting multiple species in a sample. United States patent US20050105077A1 (May 2005).
29. Zelmanovic, D., Colella, G. M., Hetherington, E. J., Chapman, E. S. and Paseltiner, L. Highly sensitive, accurate, and precise automated method and device for identifying and quantifying platelets and for determining platelet activation state using whole blood samples. U.S. Pat. No. 6,025,201A (February 2000).
30. Zelmanovic, D., Paseltiner, L. and Sorette, M. Fully automated method and reagent composition therefor for rapid identification and characterization of reticulocytes erythrocytes and platelets in whole blood. U.S. Pat. No. 6,114,173A (September 2000).
31. Zelmanovic, D., Colella, G. M., Hetherington, E. J., Chapman, E. S. and Paseltiner, L. Automated method and device for identifying and quantifying platelets and for determining platelet activation state using whole blood samples. U.S. Pat. No. 5,817,519 (October 1996).
32. Hughes Jr., H. and Schilling, R. A. Shive ratio analyser. U.S. Pat. No. 4,225,385 (September 1980).
33. Bone, R. L., Kriek, A. P., Myracle, E. D. and Rogers, D. B. Apparatus for pulp contaminant removal. U.S. Pat. No. 4,897,159 (January 1990).
34. Hill, J. Method and device for examining pulp for the presence of shives. U.S. Pat. No. 4,037,966 (June 1977).
35. Hill, J. Method and device for examining pulp for the presence of shives. U.S. Pat. No. 4,066,492 (January 1978).
36. Göhde, H. and Göhde, W. Process for automatic counting and measurement of particles. U.S. Pat. No. 4,021,117 (May 1977).
37. Von, A. G. Method of and apparatus for determining the shives content in a fiber suspension. U.S. Pat. No. 3,359,786 (December 1967).
38. Hoffmann, J. D., Gooding, R. W., Roberts, N. and Hart, R. S. System for detecting contaminants. U.S. Pat. No. 5,542,542A (August 1996).
39. Lanctot, R. and Silverwater, B. F. Device for determining the concentration of suspended solid contaminants in a fluid. U.S. Pat. No. 4,468,954 (September 1984).
40. Bedard, P., Couturier, J.-P., Boucher, J.-G. and Bedard, J. T. Particle quantifying apparatus and method. United States patent US20030142310A1 (July 2003).
41. Lehmikangas, K. and Loytynoja, L. Method for measuring particles in suspension and measuring instrument. U.S. Pat. No. 6,311,550B1 (November 2001).
42. Shields, W. R., Singh, K. M., Suska, J. F. and Macdonald, J. Measurement of paper pulp and fiber visual characteristics. U.S. Pat. No. 5,786,894 (July 1998).
43. Hughes Jr., H. and Schilling, R. A. Method for determining the relative quantity of shives in a stream of fibrous particles. U.S. Pat. No. 4,220,499 (September 1980).
44. Aikawa, Y. Device for detecting foreign matter in pulp suspension. U.S. Pat. No. 5,518,584 (May 1996).
45. Basiji, D. A. and Ortyn, W. E. Imaging and analyzing parameters of small moving objects such as cells. U.S. Pat. No. 6,249,341B1 (June 2001).
46. Nelson, A. C. and Patten, F. W. Automated cell sample enrichment preparation method. U.S. Pat. No. 7,494,809B2 (February 2009).
47. Ortyn, W. E. and Basiji, D. A. Imaging and analyzing parameters of small moving objects such as cells. U.S. Pat. No. 6,975,400B2 (December 2005).
48. Ortyn, W. E. and Basiji, D. A. Imaging and analyzing parameters of small moving objects such as cells in broad flat flow. U.S. Pat. No. 6,671,044B2 (December 2003).
49. Ortyn, W. E. and Basiji, D. A. Imaging and analyzing parameters of small moving objects such as cells. U.S. Pat. No. 7,315,357B2 (January 2008).
50. Hansen, W. P., Ferrante, A. A., Gershman, R. J., Krauledat, P. B. and Perrault Jr., D. F. System for acial pattern analysis of multicellular organisms. U.S. Pat. No. 7,116,407 B2 (October 2006).
51. Ito, Y., Toge, Y., Saito, A., Yamazaki, T. and Miyamoto, M. Method and apparatus for optically measuring specimen. U.S. Pat. No. 5,760,900 (June 1998).
52. Kain, R. C. Micro-imaging system. U.S. Pat. No. 5,754,291 (May 1998).
53. Kosaka, T. Particle analyser. U.S. Pat. No. 5,548,395 (June 1996).
54. Kosaka, T. Particle image analyzing apparatus. U.S. Pat. No. 5,159,642 (October 1992).
55. Ortyn, W. E., Seo, M. J., Basiji, D. A., Frost, K. L. and Perry, D. J. Auto focus for a flow imaging system. U.S. Pat. No. 7,087,877 (June 2006).
56. Bell, M. L., Lin, Y., Michael, J. M., Pentoney Jr., S. L. and Tsay, T.-T. Analyte detection system. U.S. Pat. No. 6,838,289B2 (January 2005).
57. Bell, M. L., Yuan, L., Michael, J. M., Pentoney Jr., S. L. and Tsay, T.-T. Analyte detection system. U.S. Pat. No. 7,300,800B2 (November 2007).
58. Noguchi, M., Tsukii, K. and Tajima, H. Small object identifying device and its identifying method. U.S. Pat. No. 7,426,027B2 (September 2008).
59. Haavig, D. L. and Lorden, G. Method and apparatus for rapid particle identification utilizing scattered light histograms. U.S. Pat. No. 6,421,121B1 (July 2002).
60. Hansen, P. W. Instrument for selecting and depositing multicellular organisms and other large objects. U.S. Pat. No. 6,657,713B2 (December 2003).
61. Noguchi, M., Tsukii, K. and Tajima, H. Small object identifying device and its identifying method. U.S. Pat. No. 7,283,229B2 (October 2007).
62. Chandler, V. S. Multi-analyte diagnostic system and computer implemented process for same. U.S. Pat. No. 6,592,822B1 (July 2003).
63. Modlin, D. N., Owicki, J. C., Petersen, J. F., French, T. E., Wright, C. L., Ruiz, J. A. and Bechtel, L. E. Multi-mode light detection system. U.S. Pat. No. 6,825,921B1 (November 2004).
64. Hairston, P. P. and Freidhoff, C. B. Systems and methods for use in detecting harmful aerosol particles. U.S. Pat. No. 7,423,751B2 (September 2008).
65. Oldham, M. F., Nordman, E. S. and Reel, R. T. Time-delay integration in a flow cytometry system. U.S. Pat. No. 7,428,047B2 (September 2008).
66. Said, A. A., Bado, P. and Dugan, M. A. Optical sensing of fluid condition-method and apparatus. U.S. Pat. No. 7,450,235B1 (November 2008).
67. Gigioli, G. W., Bope, D. W., Hairston, P. P. and Miller, E. A. Systems and methods for use in detecting harmful aerosol particles. U.S. Pat. No. 7,525,660B2 (April 2009).
68. Hairston, P. P. and Freidhoff, C. B. Systems and methods for use in detecting harmful aerosol particles. U.S. Pat. No. 7,554,663B2 (June 2009).

69. Tuschel, D. System for obtaining images in bright field and crossed polarization modes and chemical images in raman, luminescence and absorption modes. U.S. Pat. No. 7,564,541B2 (July 2009).
70. Harju, R., Salonen, J. and Turunen, H. Versatile instrumentation for optical measurement of samples. U.S. Pat. No. 7,199,879B2 (March 2007).
71. Yogi, O., Kawakami, T. and Ishikawa, M. Liquid-containing substance analyzing device and liquid-containing substance analyzing method. U.S. Pat. No. 6,881,587B2 (April 2005).
72. Birnbaum, S., Johansson, J., Larsson, P.-O., Miyabayashi, A., Mosbach, K., Nilsson, S., Svanberg, S. and Wahlund, K.-G. Method and detector for separation processes. U.S. Pat. No. 5,627,643 (May 1997).
73. Hassard, J. F., Hassard, S. and Mainwood, A. M. Molecular imaging. U.S. Pat. No. 6,613,210B1 (September 2003).
74. Sideris, D. System and method. U.S. Pat. No. 7,425,252B2 (September 2008).
75. Sideris, D. System and method. U.S. Pat. No. 7,497,934B2 (March 2009).
76. Simpson, J. W., Rothberg, J. M. and Went, G. T. Apparatus and method for the generation, separation, detection, and recognition of biopolymer fragments. U.S. Pat. No. 6,218,121B1 (April 2001).
77. Sweedler, J. V., Shear, J. B. and Zare, R. N. Method and device employing time-delayed integration for detecting sample components after separation. U.S. Pat. No. 5,141,609 (August 1992).
78. Togawa, Y. Particle size distribution measuring apparatus. U.S. Pat. No. 6,970,243B2 (November 2005).
79. Marquiss, S. A., Cesar, C. G., Petersen, J. F., Stumbo, D. P., El-Hage, A., Edwards, G. R., Modlin, D. N., Leytes, L. J. and Burd, S. Integrated sample-processing system. U.S. Pat. No. 6,838,051B1 (January 2004).
80. Frost, K. L. and Riley, J. K. Computational methods for the segmentation of images of objects from background in a flow imaging instrument. U.S. Pat. No. 7,190,832B2 (March 2007).
81. Luttermann, K., Diessel, E., Kosch, W. and Weichel, W. Process and device for the screening of molecules with regard to their individual binding behaviour towards at least one given ligand. U.S. Pat. No. 6,713,264B2 (March 2004).
82. Simpson, J. W., Rothberg, J. M. and Went, G. T. Apparatus and method for the generation, separation, detection, and recognition of biopolymer fragments. U.S. Pat. No. 6,236,945B1 (May 2001).
83. Perry, C. D., Johns, S. and Cooper, R. A. Methods To Detect Organic Contaminants In Pulp and Fiber. United States patent US20090084510A1 (April 2009).
84. Hoffmann, J. D. and Olson, J. A. Determination of contaminant particles in an aqueous pulp. U.S. Pat. No. 7,384,503B2 (June 2008).
85. Ricard, M. and Dorris, G. M., Recirculation contaminates whitewater solids Part II: Contamination of fines and fillers by extractives and metals, Presented at the 93rd PAPTAC Annual Meeting, Montreal. p. B263-B270. PAPTAC (2007).
86. Ruuska, M., Tirronen, V. and Launonen, U. Unified on-line dirt count and process disturbance analysis system for pulp applications. *Appita Journal*, 61(6) (2008).

The embodiments of the invention described above are intended to be exemplary. Those skilled in the art will therefore appreciate that the foregoing description is illustrative only, and that various alternate configurations and modifications can be devised without departing from the spirit of the present invention. Accordingly, the present invention is intended to embrace all such alternate configurations, modifications and variances which fall within the scope of the appended claims.

The invention claimed is:

1. An on-line analyser of macrocontaminants for a pulp and/or a white water stream having the macrocontaminants and fibrous material, the analyser comprising:
    a pulp classifier separating the macrocontaminants from the fibrous material in a sample of the stream into a liquid fraction comprising isolated macrocontaminants comprising light-weight and the heavy-weight macrocontaminants;
    a contaminant chamber enclosing a contaminant cell receiving the liquid fraction, wherein the light weight and the heavy weight macrocontaminants separate within the contaminant cell and the contaminant cell comprising a contaminant settling plate;
    an optical chamber comprising at least one optical detector connected to the cell capturing at least one detected image;
    a control chamber taking the at least one detected image and conducting an image analysis to determine type and quantity of at least one of the light-weight and the heavy-weight macrocontaminants in the liquid fraction;
    wherein the control chamber comprises a computer comprising a software program performing the image analysis and supervising execution of tasks of the analyser; and
    wherein the software program communicates with a camera dynamic link library, an imaging library, and an OPC server interacting to identify the type and the quantity of the at least one light-weight and the heavy-weight macrocontaminants.

2. The analyser according to claim 1, wherein the at least one optical detector is at least one high definition digital camera producing the detected image from the contaminant cell.

3. The analyser according to claim 1, wherein the contaminant settling plate comprising a coloured background optimizing the quality of the detected image.

4. The analyser according to claim 1, wherein the at least one optical detector is focused on the contaminant settling plate.

5. The analyser according to claim 1, wherein the at least one optical detector is focused at a surface of the liquid fraction within the contaminant cell.

6. The analyser according to claim 1, wherein the OPC server further communicates with PLCs communicating with the pulp classifier, contaminant chamber and the optical chamber.

7. The analyser according to claim 1, wherein the contaminant cell is a clear cylindrical cell comprising the contaminant settling plate that is an integrated coloured settling plate,
    the at least one optical detector comprising a first and a second high definition digital camera, wherein the first camera is focused on the integrated coloured settling plate and the second camera is focused on a surface of the liquid fraction, and
    the control chamber comprises a computer comprising a software program performing the image analysis and supervising execution of tasks of the analyser.

8. A method of analysing macrocontaminants from a pulp and/or white water stream having the macrocontaminants and fibrous material, the method comprising:

separating the macrocontaminants from the fibrous material in a sample from the stream into a liquid fraction of isolated macrocontaminants;

further separating the isolated macrocontaminants in the liquid fraction into light-weight and heavy-weight macrocontaminants, producing at least one detected image by optical measurement of at least one of the light-weight and the heavy-weight macrocontaminants in the liquid fraction;

analysing the at least one detected image and determining the quantity and type of at least one of the light-weight and the heavy-weight macrocontaminant in the liquid fraction; and wherein analysing the at least one detected image is with a software program of a computer communicating with a camera dynamic link library, and imaging library and an OPC server, the software program identifying the at least one macrocontaminant.

9. The method according to claim 8, wherein the at least one detected image is produced by a high definition digital camera.

10. The method according to claim 9, wherein the at least one detected image is a first detected image focused on light-weight macrocontaminants and a second detected image focused on heavy-weight macrocontaminants.

11. The method of claim 10, wherein the software program further communicates with the OPC server to control the separating of the sample and the producing the at least one detected image.

12. The method of claim 8, wherein the heavy-weight macrocontaminants are selected from the group consisting of macrostickies, shives, hotmelts, high-density plastics, varnishes, black contaminants and combinations thereof.

13. The method of claim 8, where the light-weight macrocontaminants are selected from the group consisting of waxes, low-density stickies, hotmelts, plastics, varnishes and combinations thereof.

* * * * *